(12) United States Patent
Chiu et al.

(10) Patent No.: US 11,453,008 B2
(45) Date of Patent: Sep. 27, 2022

(54) DEVICE FOR SORTING BIO-PARTICLES USING IMAGE-MANIPULATED ELECTRIC FORCE AND OPERATING METHOD THEREOF

(71) Applicant: Ace Medical Technology Co., Ltd., Taipei (TW)

(72) Inventors: Tzu-Keng Chiu, New Taipei (TW); Yu-Xian Zhu, Hsinchu County (TW); Huan-Yi Tseng, New Taipei (TW)

(73) Assignee: Ace Medical Technology Co., Ltd., Taipei (TW)

( * ) Notice: Subject to any disclaimer, the term of this patent is extended or adjusted under 35 U.S.C. 154(b) by 153 days.

(21) Appl. No.: 16/822,033

(22) Filed: Mar. 18, 2020

(65) Prior Publication Data

US 2020/0230605 A1 Jul. 23, 2020

Related U.S. Application Data

(60) Provisional application No. 62/820,817, filed on Mar. 19, 2019.

(30) Foreign Application Priority Data

Apr. 30, 2019 (EP) .................................... 19171783

(51) Int. Cl.
*B01L 3/00* (2006.01)
*B03C 5/00* (2006.01)
(Continued)

(52) U.S. Cl.
CPC ........ *B01L 3/502761* (2013.01); *B03C 5/005* (2013.01); *C12N 13/00* (2013.01);
(Continued)

(58) Field of Classification Search
CPC ......... B01L 3/502761; B01L 2200/027; B01L 2200/0652; B01L 2400/0424;
(Continued)

(56) References Cited

U.S. PATENT DOCUMENTS

| 6,432,630 B1 | 8/2002 | Blankenstein |
|---|---|---|
| 7,612,355 B2 | 11/2009 | Wu |

(Continued)

FOREIGN PATENT DOCUMENTS

| CN | 101623660 A | 1/2010 |
|---|---|---|
| CN | 102449163 A | 5/2012 |

(Continued)

OTHER PUBLICATIONS

Chiu et al (Optically-induced-dielectrophoresis (ODEP)-based cell manipulation in a microfluidic system for high-purity isolation of integral circulating tumor cell (CTC) clusters based on their size characteristics, Sensors and Actuators B: Chemical, Available Online Dec. 7, 2017, pp. 1161-1173) (Year: 2017).*

(Continued)

*Primary Examiner* — Benjamin R Whatley
*Assistant Examiner* — Jean Caraballo-Leon
(74) *Attorney, Agent, or Firm* — Winston Hsu

(57) ABSTRACT

A device for sorting bio-particles by image-manipulated electric force includes a first substrate, a second substrate, a fluidic channel, one or more photosensitive layers and an inlet hole. The first substrate has a first conductive electrode, and the second substrate has a second conductive electrode. The second conductive electrode is disposed opposite the first conductive electrode. The fluidic channel is disposed between the first conductive electrode and the second conductive electrode. The photosensitive layer is conformally disposed on at least one of the surfaces of the first conductive electrode and the second conductive electrode. The inlet (Continued)

hole is disposed in the first conductive electrode and the first substrate, where the inlet hole includes a first opening close to the fluidic channel and a second opening away from the fluidic channel, and the surface area of the first opening is greater than the surface area of the second opening.

18 Claims, 22 Drawing Sheets

(51) Int. Cl.
  *C12N 13/00* (2006.01)
  *C12N 5/09* (2010.01)
(52) U.S. Cl.
  CPC . *B01L 2200/027* (2013.01); *B01L 2200/0652* (2013.01); *B01L 2400/0424* (2013.01); *B03C 2201/26* (2013.01); *C12N 5/0693* (2013.01)
(58) Field of Classification Search
  CPC ..... B01L 2300/0645; B01L 2300/0654; B01L 2300/0816; B01L 2300/0864; B01L 2300/0887; B01L 2400/0454; B01L 3/50273; B03C 5/005; B03C 2201/26; B03C 5/026; C12N 13/00; C12N 5/0693; C12M 23/16; C12M 35/02
  See application file for complete search history.

(56) References Cited

U.S. PATENT DOCUMENTS

| | | | |
|---|---|---|---|
| 9,630,180 B2 | 4/2017 | Srinivasan | |
| 2002/0182627 A1 | 12/2002 | Wang | |
| 2003/0096081 A1 | 5/2003 | Lavallee | |
| 2004/0023273 A1 | 2/2004 | Puget | |
| 2007/0207548 A1 | 9/2007 | Blankenstein | |
| 2009/0032449 A1 | 2/2009 | Mueth | |
| 2009/0170186 A1 | 7/2009 | Wu | |
| 2012/0118740 A1 | 5/2012 | Garcia | |
| 2012/0190040 A1 | 7/2012 | Talebpour | |
| 2012/0295343 A1 | 11/2012 | Bear | |
| 2014/0008230 A1* | 1/2014 | Chen | B03C 5/024 204/643 |
| 2014/0044610 A1 | 2/2014 | Miyoshi | |
| 2015/0151307 A1 | 6/2015 | Breinlinger | |
| 2017/0297036 A1 | 10/2017 | Wu | |
| 2018/0120255 A1 | 5/2018 | Wu | |

FOREIGN PATENT DOCUMENTS

| | | | | |
|---|---|---|---|---|
| CN | 103890397 A | * | 6/2014 | ......... B01J 19/0093 |
| CN | 105736330 A | | 7/2016 | |
| CN | 107999281 A | | 5/2018 | |
| CN | 108007849 A | | 5/2018 | |
| JP | 2002-503334 A | | 1/2002 | |
| JP | 2007-537729 A | | 12/2007 | |
| JP | 2012-522518 A | | 9/2012 | |
| JP | 2014-55940 A | | 3/2014 | |
| JP | 2016-105732 A | | 6/2016 | |
| JP | 2016-539631 A | | 12/2016 | |
| JP | 2017-166989 A | | 9/2017 | |
| TW | 201833544 A | | 9/2018 | |
| WO | 2005/100541 A2 | | 10/2005 | |

OTHER PUBLICATIONS

Huang Di et al., "Microfluidics-Based Circulating Tumor Cells Separation", Jul. 1, 2015, pp. 882-912, Progress in Chemistry, Nanjing.

* cited by examiner

DEVICE FOR SORTING BIO-PARTICLES USING IMAGE-MANIPULATED ELECTRIC FORCE AND OPERATING METHOD THEREOF

CROSS REFERENCE TO RELATED APPLICATIONS

This application claims the benefit of U.S. provisional patent application Ser. No. 62/820,817, filed on 2019 Mar. 19, the disclosure of which is incorporated herein by reference in its entirety.

BACKGROUND OF THE INVENTION

1. Field of the Invention

The present disclosure relates generally to the field of sorting bio-particles, and more particularly, to the field of sorting bio-particles from fluid heterogeneous mixtures by using image-manipulated electric force.

2. Description of the Prior Art

Over the past few decades, various approaches to effectively diagnosing, detecting, and/or treating cancer have been studied and disclosed by several academic institutions or companies. Also, a number of researches have been conducted in order to target or kill cancer in vivo. However, only limited solutions are feasible due to the uncertainty and variability of cancer.

One of the approaches to diagnosing and detecting cancer is by sorting and isolating specific cancer-related cells in vitro. These cells may be circulating tumor cells (CTCs) which are generated during metastasis within the host's body. U.S. Patent application (US 2017/0297036) discloses a method of detecting and sorting CTCs in a microfluidic device using light-induced dielectrophoresis. The microfluidic device includes a microfluidic channel inside which fluid is able to flow. During the sorting process, a fluid containing cells is injected into the microfluidic channel, and a cell to be sorted is then identified and positioned when the cell reaches a predetermined region. Then, a ring-shaped light zone is illuminated on the identified and positioned cell. Afterwards, a bar-shaped light zone is illuminated on the microfluidic channel and moved from one side to the other side of the microfluidic channel. During the movement of the bar-shaped light zone, unwanted cells in the microfluidic channel are swept away by the edge of the bar-shaped light zone due to non-uniform electric field generated near the edge of the bar-shaped light zone. In contrast, during the movement of the bar-shaped light zone, the cell to be sorted which overlaps the ring-shaped the light zone is not swept away and thus is able to remain at its original position. Finally, after all the unwanted cells are swept away, the cell to be sorted may be further moved to a collecting region by moving the ring-shaped light zone so as to complete a single sorting process. The sorting process may be repeated several times until all of the cells to be sorted are collected completely.

Even though the sorting process disclosed in US 2017/0297036 is able to sort specific cells, such as CTCs, there are still some drawbacks need to be overcome. For example, the time used for sorting each cell is relatively long. Besides, unwanted cells may not be swept away completely by the light bar and thus some of the unwanted cells may flow into the collecting region along with the cells to be sorted.

Furthermore, since the fluid containing heterogeneous mixtures is injected into the microfluidic channel through an inlet, it is inevitable that some of the cells in the fluid may adhere or stock to the inner surface of the microfluidic channel near the inlet, which also negatively affects the accuracy of the sorting process.

SUMMARY OF THE INVENTION

To this end, the present disclosure aims at providing a sorting device by using image-manipulated electric force and a method of operating the same that are able to increase the time efficiency and the accuracy of a sorting process.

In some embodiments, a device for sorting bio-particles by image-manipulated electric force includes a first substrate, a second substrate, a fluidic channel, one or more photosensitive layers and an inlet hole. The first substrate has a first conductive electrode, and the second substrate has a second conductive electrode. The second conductive electrode is disposed opposite the first conductive electrode. The fluidic channel is disposed between the first conductive electrode and the second conductive electrode. The photosensitive layer is conformally disposed on at least one of the surfaces of the first conductive electrode and the second conductive electrode. The inlet hole is disposed in the first conductive electrode, where the inlet hole includes a first opening close to the fluidic channel and a second opening away from the fluidic channel, and the surface area of the first opening is greater than the surface area of the second opening.

In some embodiments, a method of operating an apparatus including the above-mentioned sorting device includes the steps of (a) providing a liquid including bio-particles to a fluidic channel through an inlet hole; (b) identifying the bio-particles when the bio-particles flows to a sorting region of the fluidic channel; (c) reducing the flowing rate of the liquid or stopping the flow of the liquid after the bio-particles are identified; (d) positioning the bio-particles after step (c);(e) illuminating a light zone on the sorting region, where the area of the light zone is greater than half of the area of the main channel; (f) illuminating a light pattern with a dark zone on the sorting region when the sorting region is illuminated by the light zone, where the light pattern overlaps at least one of the bio-particles, and the dark zone has a luminance darker than a luminance of a region adjacent to the dark zone; and (g) moving the bio-particle overlapping the light pattern.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

In the following, the invention is further illustrated by way of example, taking reference to the accompanying drawings. Thereof.

DETAILED DESCRIPTION

This specification describes exemplary embodiments and applications of the disclosure. The disclosure, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation.

It should be noted that, the term "image-manipulated electric force" may be regarded as force generated from light-induced dielectrophoresis. That is to say, the method of manipulating bio-particles disclosed in the present application may be regarded as a type of method of manipulating bio-particles by light-induced dielectrophoresis.

Figure 1:
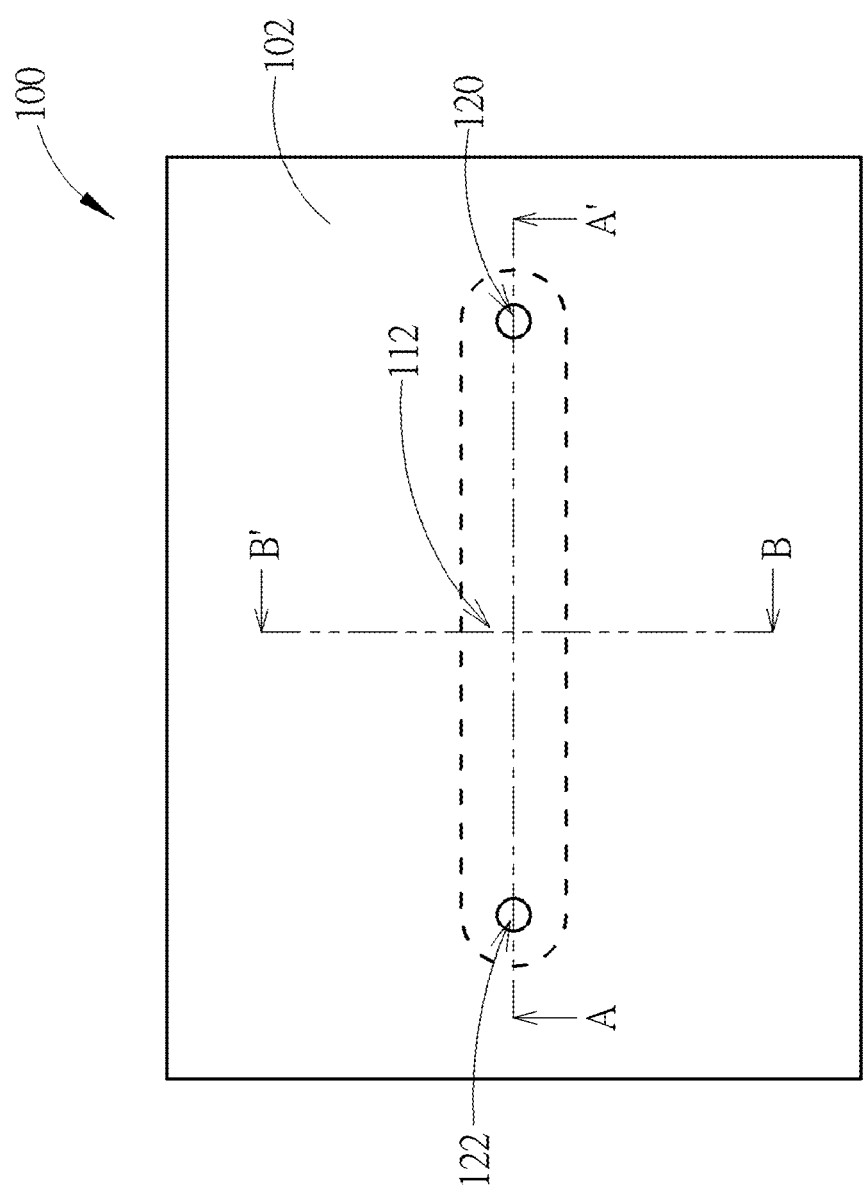
FIG. 1 is a schematic top view of a device for sorting bio-particles from fluid heterogeneous mixture according to one embodiment of the present disclosure.

FIG. 1 is a schematic top view of a device for sorting bio-particles from fluid heterogeneous mixture according to one embodiment of the present disclosure. A device 100 includes two opposing substrates, such as an upper cover 102 and a lower cover (not shown). A microfluidic channel, such as a main channel 112, is disposed between the covers. Two accesses, such as an inlet 120 and an outlet 122, are disposed at two distal ends of the main channel 112. During the process of operating the device 100, a liquid mixture containing bio-particles, such as cells, and liquid medium may be injected into the main channel 112 through the inlet 120 and drained from the main channel 112 through the outlet 122. Although the upper cover 102 shown in FIG. 1 is of a rectangle, the shape of the upper cover 102 (or the lower cover) may be modified properly in order to fulfill different requirements. Thus, the upper cover 102 (or the lower cover) may be of triangle, square, circle, rectangle, multi angle, but not limited thereto.

Figure 2:
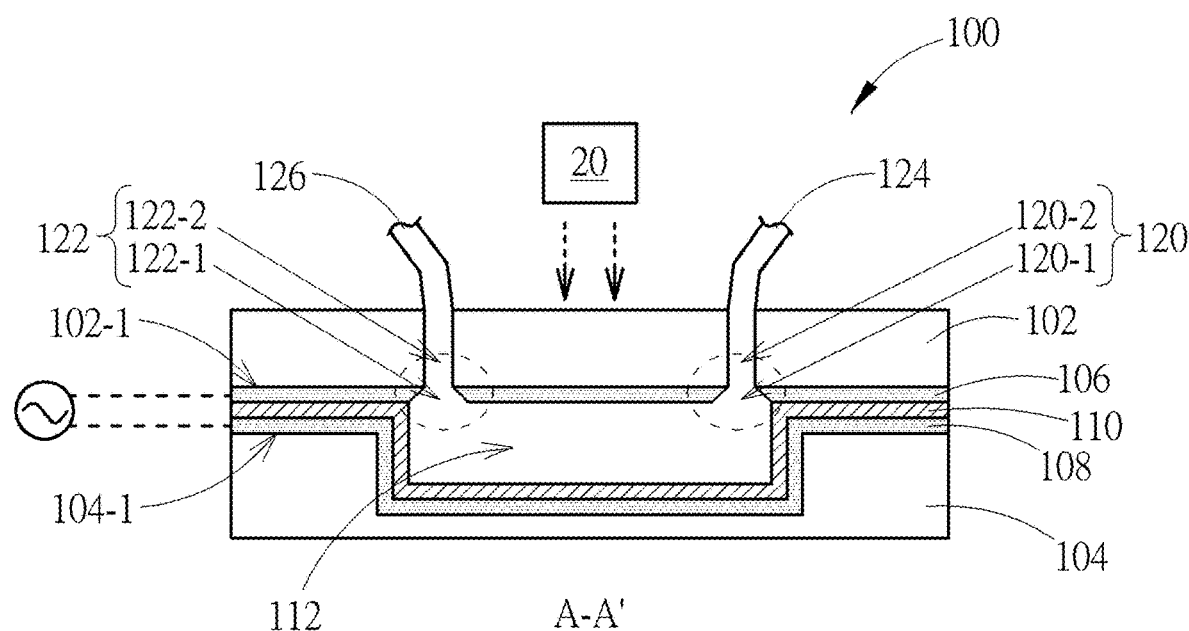
FIG. 2 shows cross-sectional diagrams respectively taken along line A-A' and line B-B' of FIG. 1 according to one embodiment of the disclosure.
Figure 2:
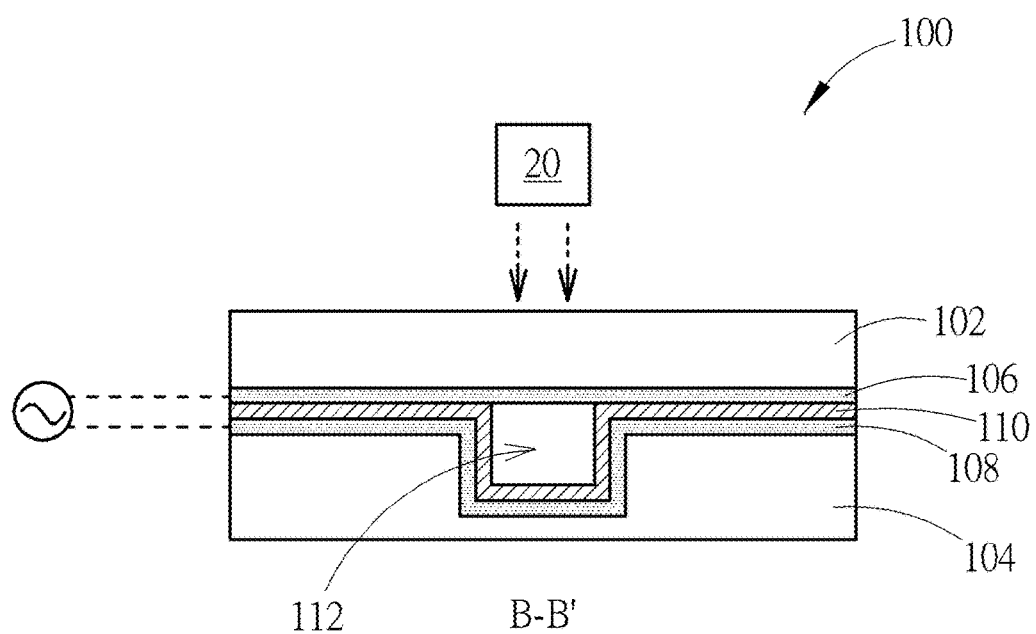

FIG. 2 shows two cross-sectional diagrams respectively taken along line A-A' and line B-B' of FIG. 1 according to one embodiment of the disclosure. The device 100 includes the upper cover 102, the lower cover 104 disposed opposite the upper cover 102, and a photosensitive material 110 disposed between the upper cover 102 and the lower cover 104. At least two transparent conductive electrodes, such as a first transparent conductive electrode 106 and a second transparent conductive electrode 108, are respectively deposited or coated on the inner surfaces 102-1 of the upper cover 102 and the inner surface 104-1 of the lower cover 104. The first transparent conductive electrode 106 and the second transparent conductive electrode 108 may be made of transparent conductive material, such as indium tin oxide (ITO) or indium zinc oxide (IZO), but not limited thereto, and may be electrically coupled to an AC generator, so that an alternating electrical field may be generated in the main channel 112 between the two opposing electrodes 106 and 108 when the AC generator is turned on. The thickness of the first transparent conductive electrode 106 and the thickness of the second transparent conductive electrode 108 may be respectively at a range of 0.05-0.4 μm.

The first transparent conductive electrode 106 and the second transparent conductive electrode 108 may be separated from each other by the photosensitive material 110, which may be made of hydrogenated amorphous silicon (a-Si:H), but is not limited thereto. Light source 20, which is able to illuminate light of required wavelength onto the photosensitive material 110, may be placed above or under the device 100. When light is illuminated on the photosensitive material 110, charges may be generated and accumulated in the region being illuminated. Thus, the electrical conductivity of the photosensitive material 110 may be changed by illuminating light on it. The thickness of the photosensitive material 110 may be in a range of 0.1-2 µm, and preferably in a range of 0.5-1 µm. It should be noted that, although the first transparent conductive electrode 106 is in direct contact with the photosensitive material 110, the first transparent conductive electrode 106 may be separated from the photosensitive material 110 by disposing another electrically isolated layer according to other embodiments of the present disclosure.

As alternative, the above-mentioned upper cover 102 and the lower cover 104 may be made of glass, polymethyl-methacrylate (PMMA), polydimethylsiloxane (PDMS), metal, cyclic olefin copolymer, and cyclic olefin polymers, but not limited thereto. Also, the first transparent conductive electrode 106 and the second transparent conductive electrode 108 may be made of transparent conducting films, indium tin oxide, transparent conductive oxides, conductive polymers, metal grids and random metallic networks, carbon nanotubes, graphene, nanowire meshes, and ultra-thin metal films, but not limited thereto. The photosensitive material 110 may be made of metal nanoparticles, graphene, amorphous silicon, molybdenum disulfide, indium arsenide nanowires, but not limited thereto.

The main channel 112 is disposed between the upper cover 102 and the lower cover 104, and the contour of portions of the main channel 112 (including the sidewalls and the bottom surface of the main channel 112) may be defined by the surface of the photosensitive material 110. Preferably, the ratio of the width of the main channel 112 to the average diameter of the bio-particles flowing in the main channel 112 may be from 1:1 to 200:1, but not limited thereto. An inlet tube 124 is connected to an inlet 120 of the device 100, and an outlet tube 126 is connected to an outlet 122 of the device 100. The inlet 120 may include two parts: an inlet hole 120-1 and a through hole 120-2. Also, the outlet 122 may include two parts: an outlet hole 122-1 and a through hole 122-2. Both the inlet hole 120-1 and the outlet hole 122-1 may be disposed in the first transparent conductive electrode 106, and both the through holes 120-2 and 122-2 may be disposed in the upper cover 102. For the inlet hole 120-1 and the outlet hole 122-1, each of the holes may include two openings with different opening areas. It should be noted that, although the inlet hole 120-1 and the outlet hole 122-1 are disposed in the first transparent conductive electrode 106 according to this embodiment, each of the inlet hole 120-1 and the outlet hole 122-1 may also extend to the upper cover 102. As a result, each of the inlet hole 120-1 and the outlet hole 122-1 may be partly disposed in the upper cover 102.

Figure 3:
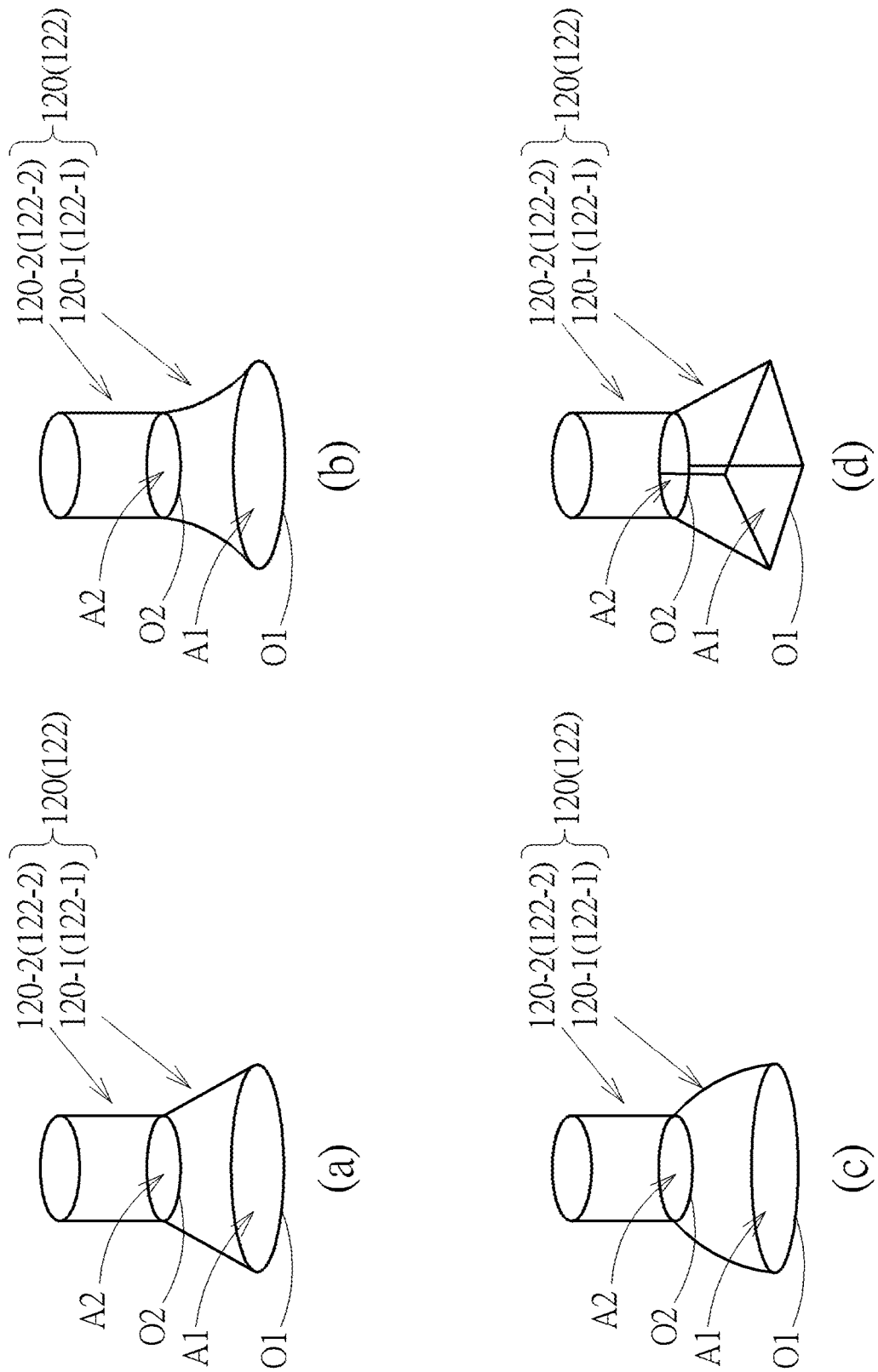
FIG. 3 is a schematic diagram of various types of inlets and outlets according to one embodiment of the present disclosure.

FIG. 3 is a schematic diagram of various types of inlets and outlets according to some embodiments of the present disclosure. For each of the inlet 120 and outlet 122 (such as types (a) to (d)), the inlet hole 120-1 (or outlet hole 122-1) includes a first opening O1 close to the main channel 112 and a second opening O2 away from the main channel 112. The surface area A1 of the first opening O1 is greater than the surface area A2 of the second opening O2. The common feature of the inlets 120 and outlets 122 shown in FIG. 3 is that the cross-sectional area is gradually increased from the second opening O2 to the first opening O1. Due to the feature "the gradually increased cross-sectional area", when the liquid mixture containing the bio-particles flows into or out of the main channel 112, the bio-particles are less likely to be adhered or stocked on the surface of the opening of the inlet 120 and outlet 122 near the main channel 112. The second opening O2 may be disposed in the first conductive electrode or in the upper cover depending on different requirements.

Figure 4:
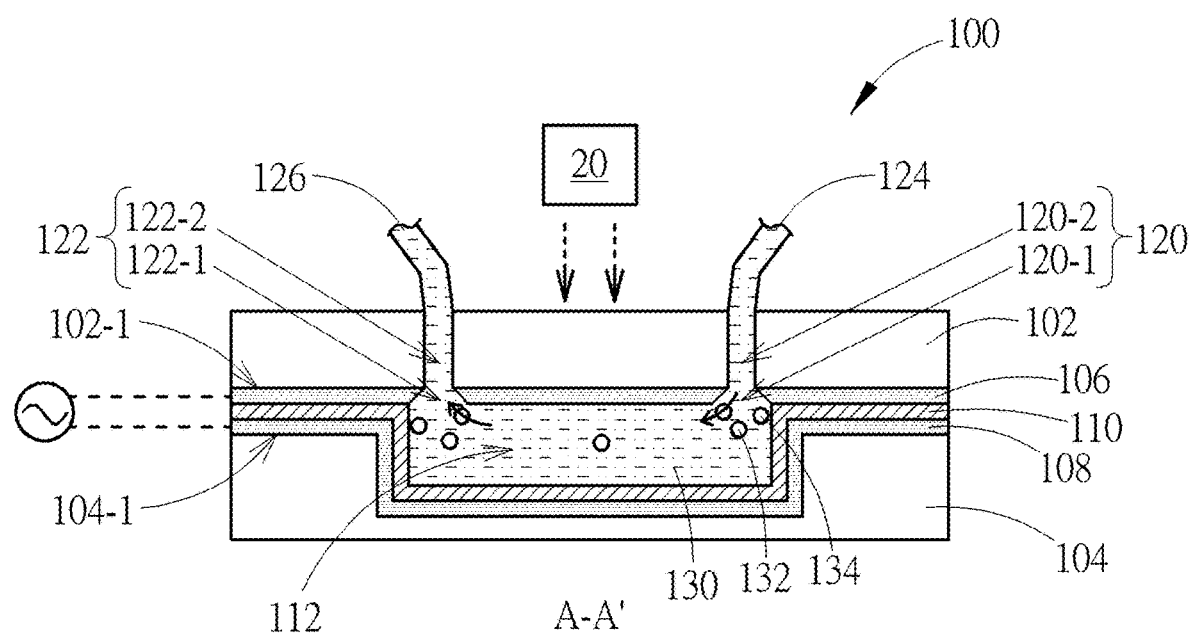
FIG. 4 is a schematic diagram showing a sorting device during a process of transporting a fluid heterogeneous mixture transports in a main channel of the device according to one embodiment of the disclosure.

FIG. 4 is a schematic diagram showing a sorting device during a process of transporting a fluid heterogeneous mixture through a main channel according to one embodiment of the disclosure. A fluid heterogeneous mixture 130 being injected into the main channel 112 may include different types of bio-particles, such as circulating tumor cells 132 and blood cells 134. Due to the feature that the cross-sectional area A1 of the opening O1 near the main channel 112 is greater than the cross-sectional area A2 of the opening O2 away from the main channel 112, these cells 132 and 134 may easily flow into or out of the inlet 120 and outlet 122, and would not adhere to or stock near the openings O1. As a result, the accuracy and the efficiency of the sorting process may be increased since all of the cells 132 and 134 in the fluid heterogeneous mixture 130 may successfully flow through the main channel 112 and be discharged by the outlet tube 126. Since the thickness of first transparent conductive electrode 106 is relatively thin, e.g. 0.05-0.4 µm, the openings O2 of the inlet hole 120-1 and outlet hole 122-1 are preferably disposed in the upper cover 102 according to some embodiments of the present disclosure.

Figure 5:
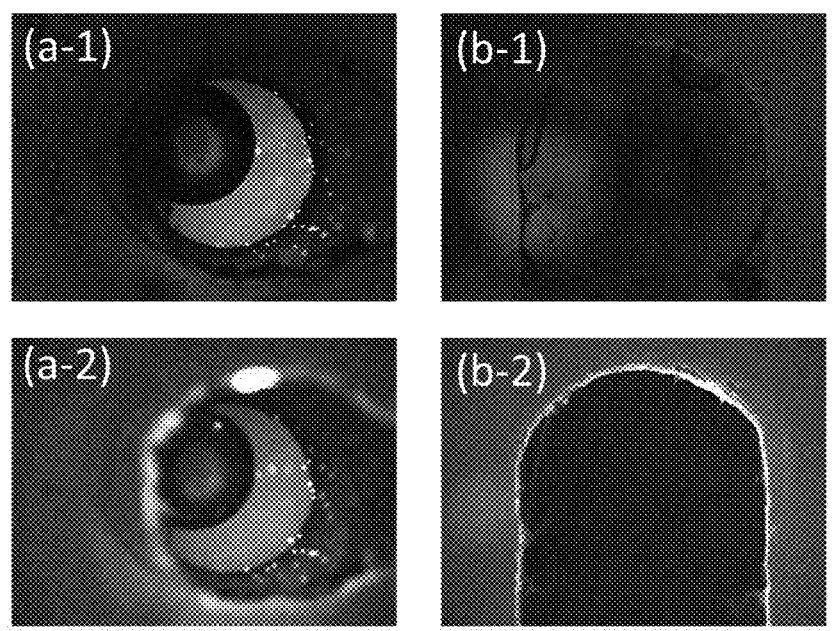
FIG. 5 shows a result of operating sorting devices having different types of inlets and outlets.

FIG. 5 demonstrates a result of operating sorting devices having different types of inlets and outlets. Photographs (a-1) and (a-2) are taken at an opening of an inlet (or outlet) of a conventional sorting device during the process of flowing fluid heterogeneous mixture into or out of the device. The bright dots in the photographs represent cells, and these cells are obviously adhered or stocked at the inlet or outlet. In contrast, photographs (b-1) and (b-2) are taken at an opening of an inlet (or outlet) of a sorting device according to one embodiment of the present invention. None of the bright dots is shown in photographs (b-1) and (b-2), which means that none of the cells is adhered or stocked at the inlet or outlet.

As alternative, the types of bio-particles disclosed herein are not limited to cells and may also be replaced with tumor cells, stem cells, blood cells, neuron cells, epithelial cells, immune cells, Induced pluripotent stem (iPS) cells, bacterium comprising gram-positive bacterium, gram-negative bacterium, virus, exsosome, liposomes with RNA, DNA, or protein, parasite, or any other biologically related particles, but not limited thereto.

Figure 6:
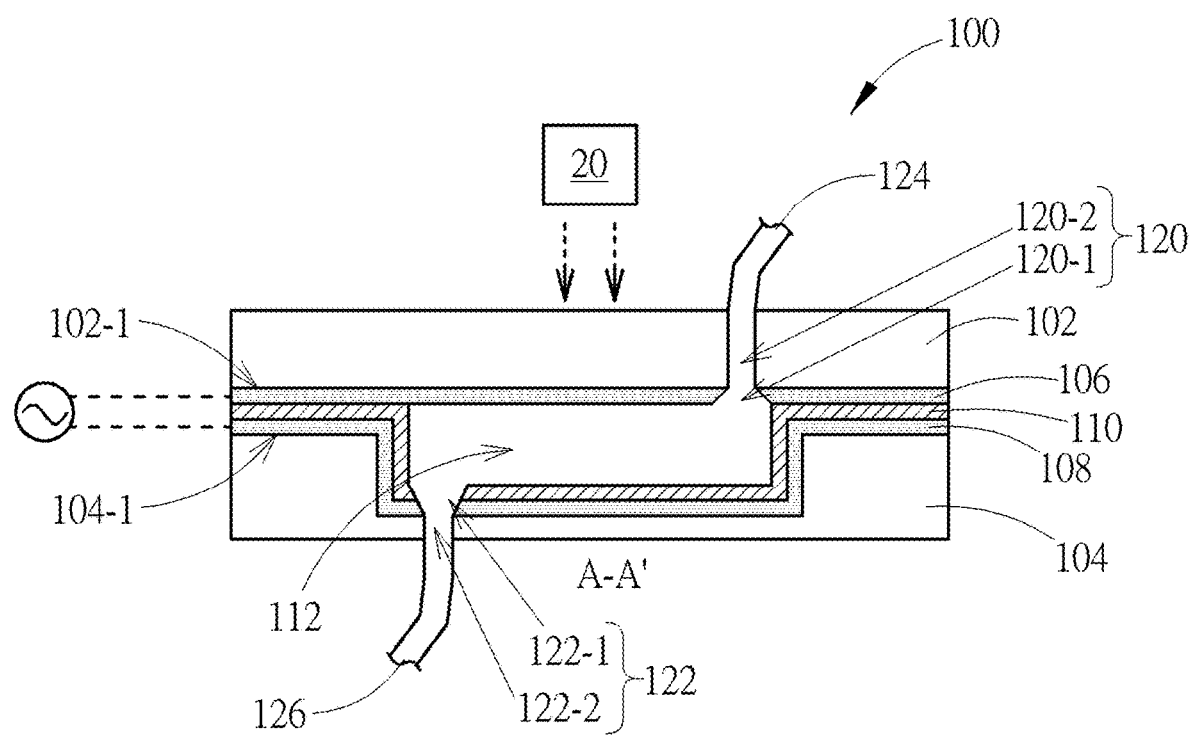
FIG. 6 is a schematic diagram showing a device having an outlet opposite to an inlet where the outlet and the inlet are disposed at two ends of a main channel according to another embodiment of the present disclosure.

FIG. 6 is a schematic diagram showing a device having an outlet opposite an inlet where the outlet and inlet are disposed at two ends of a main channel according to another embodiment of the present disclosure. The device 100 shown in FIG. 6 also includes the upper cover 102, the lower cover 104, two conductive electrodes 106 and 108, and the photosensitive material 110. The main difference between the structures shown in FIG. 6 and FIG. 2 is that the outlet hole 122-1 of FIG. 6 is disposed in the second conductive electrode 108 and may further extend to the photosensitive material rather than in the first conductive electrode 106. That is to say, the fluid mixture entering the device 100 may flow out of the device 100 through the end of the main channel 112. Therefore, the space arrangement of the device can be set properly. Also, outlet hole 122-1 may further extend to the lower cover 104 depending on different requirements.

Figure 7:
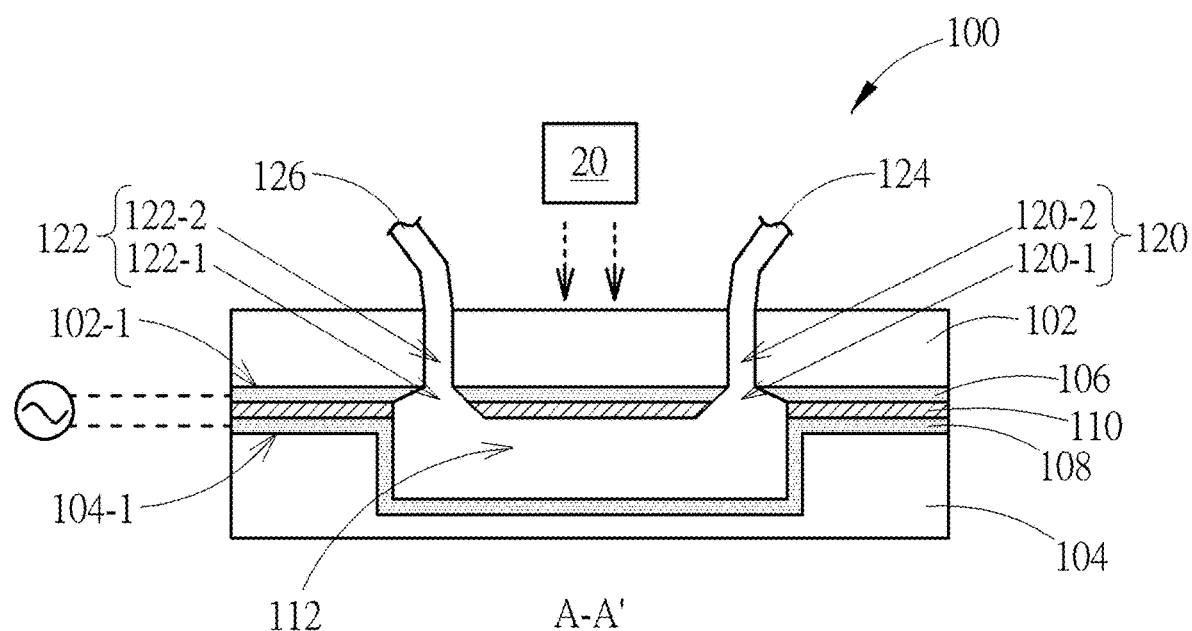
FIG. 7 is a schematic diagram showing a device having a photosensitive layer on the top of a main channel according to another embodiment of the present disclosure.
Figure 7:
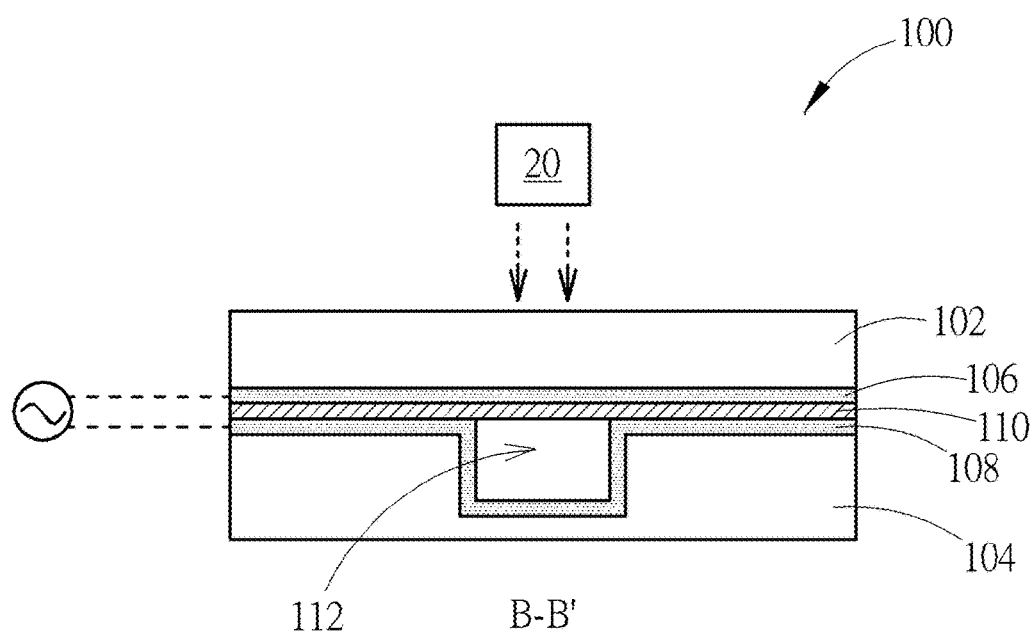

FIG. 7 is a schematic diagram showing a device having a photosensitive layer on the top of a main channel according to another embodiment of the present disclosure. The device 100 shown in FIG. 7 is similar to that shown in FIG. 2, the main difference is that the photosensitive material 110 shown in FIG. 7 is conformally disposed on the first transparent conductive electrode 106 rather than on the second transparent conductive electrode 108. Thus, the bottom surface of the main channel 112 is not in direct contact with the photosensitive material 110. In contrast, the top surface of the main channel 112 is in direct contact with the photosensitive material 110 according to this embodiment.

Figure 8:
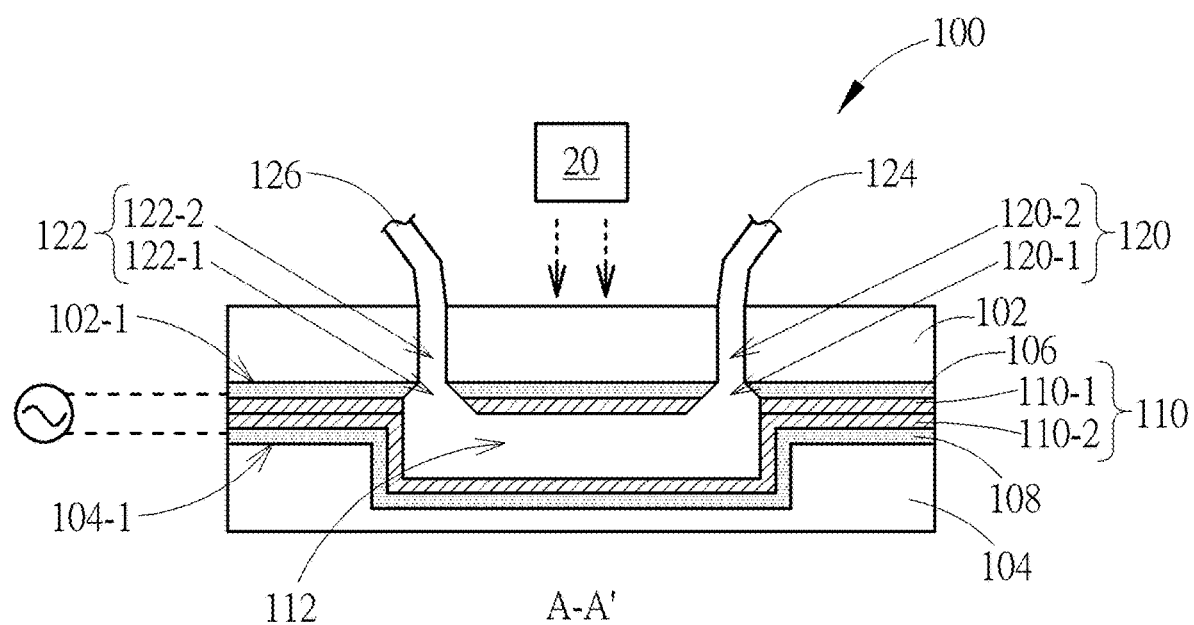
FIG. 8 is a schematic diagram showing a device having two layers of photosensitive material according to another embodiment of the present invention.

FIG. 8 is a schematic diagram showing a device having two layers of photosensitive material according to another embodiment of the present disclosure. The device 100 shown in FIG. 8 is similar to that shown in FIG. 2, the main difference between these two embodiments is that two layers of photosensitive material 110-1 and 110-2 are respectively conformally disposed on the first transparent conductive electrode 106 and the second transparent conductive electrode 108. Thus, the bottom surface and the top surface of the main channel 112 are in direct contact with the photosensitive material 110.

Figure 9:
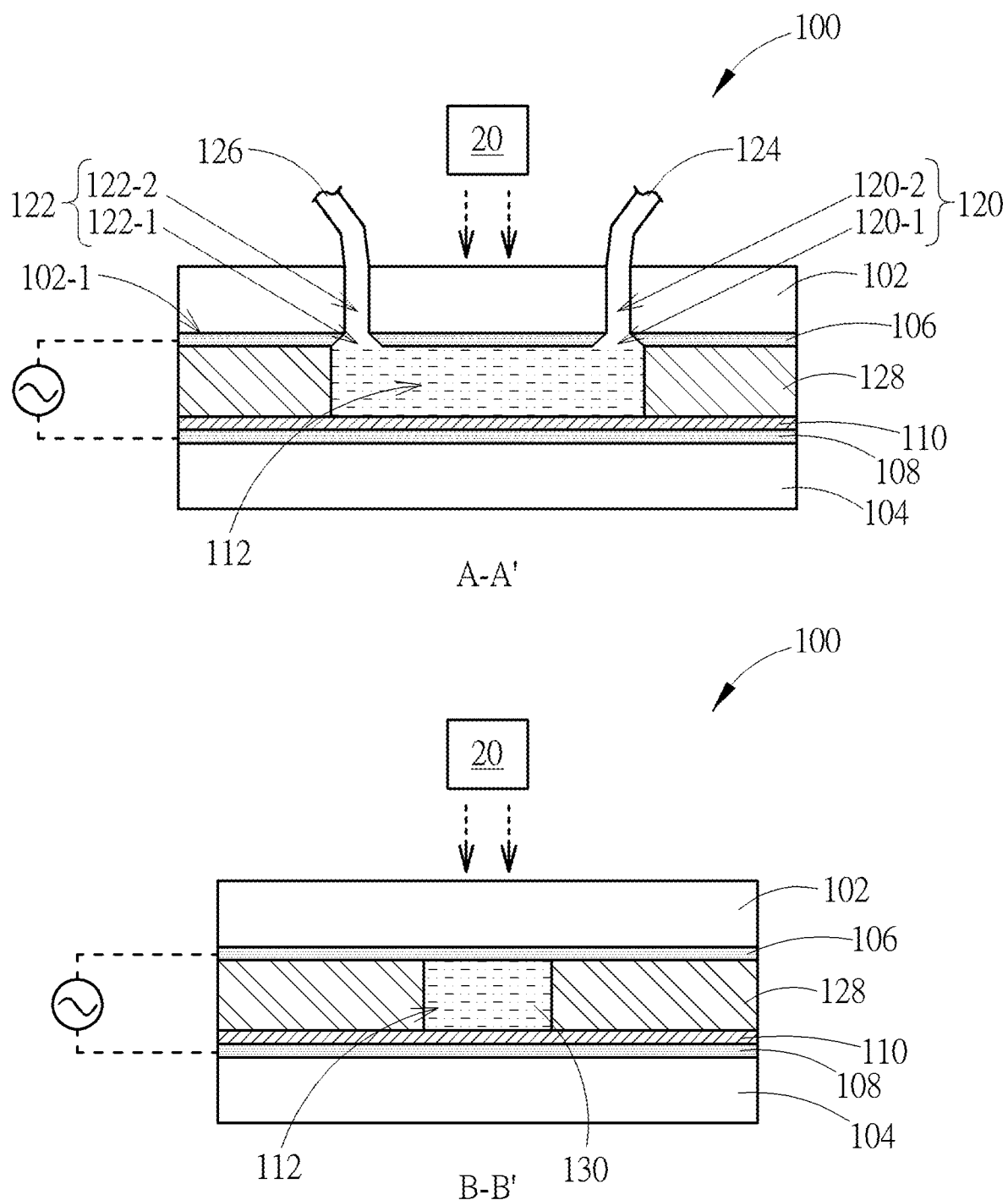
FIG. 9 is a schematic diagram showing a device having an intermediate layer according to another embodiment of the present disclosure.

FIG. 9 is a schematic diagram showing a device having an intermediate layer according to another embodiment of the present disclosure. The device 100 shown in FIG. 9 is similar to that shown in FIG. 2, the main difference between these two embodiments is that an intermediate layer 128 is further disposed between the upper cover 102 and the lower cover 104, and more preferably disposed between the first transparent conductive electrode 106 and the photosensitive material 110. In one embodiment, the main channel 112 is set in the intermediate layer 128 and may be regarded as a cavity fabricated in the intermediate layer 128. Additional adhesives may be disposed between the intermediate layer 128 and the upper and lower covers 102 and 104 so that the intermediate layer 128 may be adhered to the upper cover 102 and the lower cover 104. The intermediate layer 128 may be made of electrically isolating material used to separate the upper cover 102 and the lower cover 104. Besides, the intermediate layer 128 may be a semipermeable membrane which allows extra ions inside the fluid heterogeneous mixture 130 to diffuse out of the main channel 112. During the process of transporting the fluid heterogeneous mixture 130 in the main channel 112, some of the weak cells in the fluid heterogeneous mixture 130 may be broken. Additional ions may be released from the broken or broken dead cells into the fluid heterogeneous mixture 130, which negatively affects the electrical conductivity of the fluid heterogeneous mixture 130 and thus affects the image-manipulated electric force for moving cells. Therefore, by disposing the intermediate layer 128 made of semipermeable material, the additional ions may be able to flow out of the main channel 112 through the semipermeable material so as to maintain the electrical conductivity of the fluid heterogeneous mixture 130 at a certain level.

Still, the intermediate layer 128 shown in FIG. 9 may be made of biocompatible material which does not react or dissolve harmful materials with the cells or liquid medium of the fluid heterogeneous mixture 130. Thus, the cells flowing in the main channel 112 may not be contaminated by the main channel 112. As an example, biocompatible material may be further conformally disposed along the sidewall. Furthermore, the intermediate layer 128 or the main channel 112 may be made by the biocompatible material if required.

Figure 10:
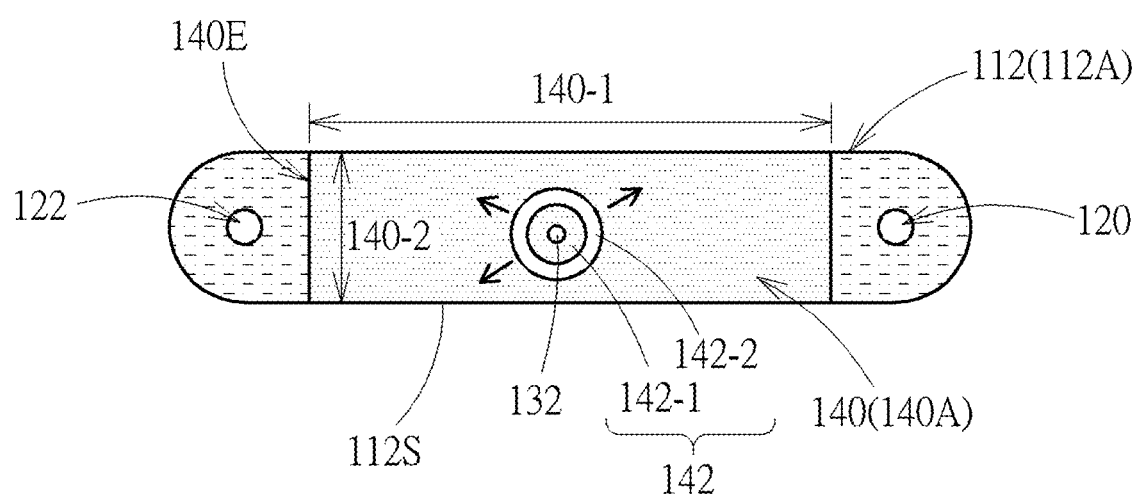
FIG. 10 is a schematic diagram showing a method of manipulating bio-particles in a device by using image-manipulated electric force according to one embodiment of the present disclosure.

FIG. 10 is a schematic diagram showing a method of manipulating bio-particles in a device by using image-manipulated electric force according to one embodiment of the present disclosure. During the operation of the device, an alternating electrical field is applied between the two opposing transparent electrodes so as to polarize the cell 132 flowing in the main channel 112. When the polarized cell 132 flows to a predetermined region of the main channel 112, the light source may illuminate a light on the photosensitive material in the predetermined region so as to generate a light zone 140 in the main channel 112. The predetermined region may be any region that can be observed by an optical microscope or a fluorescence microscope, but not limited thereto. Also, a light pattern 142 including an inner light zone 142-1 and an outer dark zone 142-2 is illuminated on the photosensitive material where the cell 132 exists. The inner light zone 142-1 may be a circular light zone, and the outer dark zone 142-2 may be a ring-shaped dark zone, but are not limited thereto. Since there is an electrical field gradient at the border 144*b* of the inner light zone 142-1 and the outer dark zone 142-2, the cell 132 may be confined in the inner light zone 142-1 and moved along with the light zone 140 during the process of moving the light pattern 142. Besides, the surface area 140A of the light zone 140 (defined by the length 140-1 and the width 140-2 of the light zone 140) is preferably greater than half of the area 112A of the main channel 112 (defined by the sidewall 112S of the main channel 112). It should be noted that, electrical field gradient may also be generated on the edge 140E of the light zone 140 so that other cells not overlapping the light pattern 142 may be kept in the light zone 140. The term "dark zone" described herein may refer to a region whose luminance is less than the luminance of adjacent regions, while the term "light zone" described herein may refer a region whose luminance is greater than the luminance of adjacent regions. Therefore, the outer dark zone 142-2 may also be illuminated by light as long as the outer dark zone 142-2 is kept darker than adjacent regions.

Figure 11:
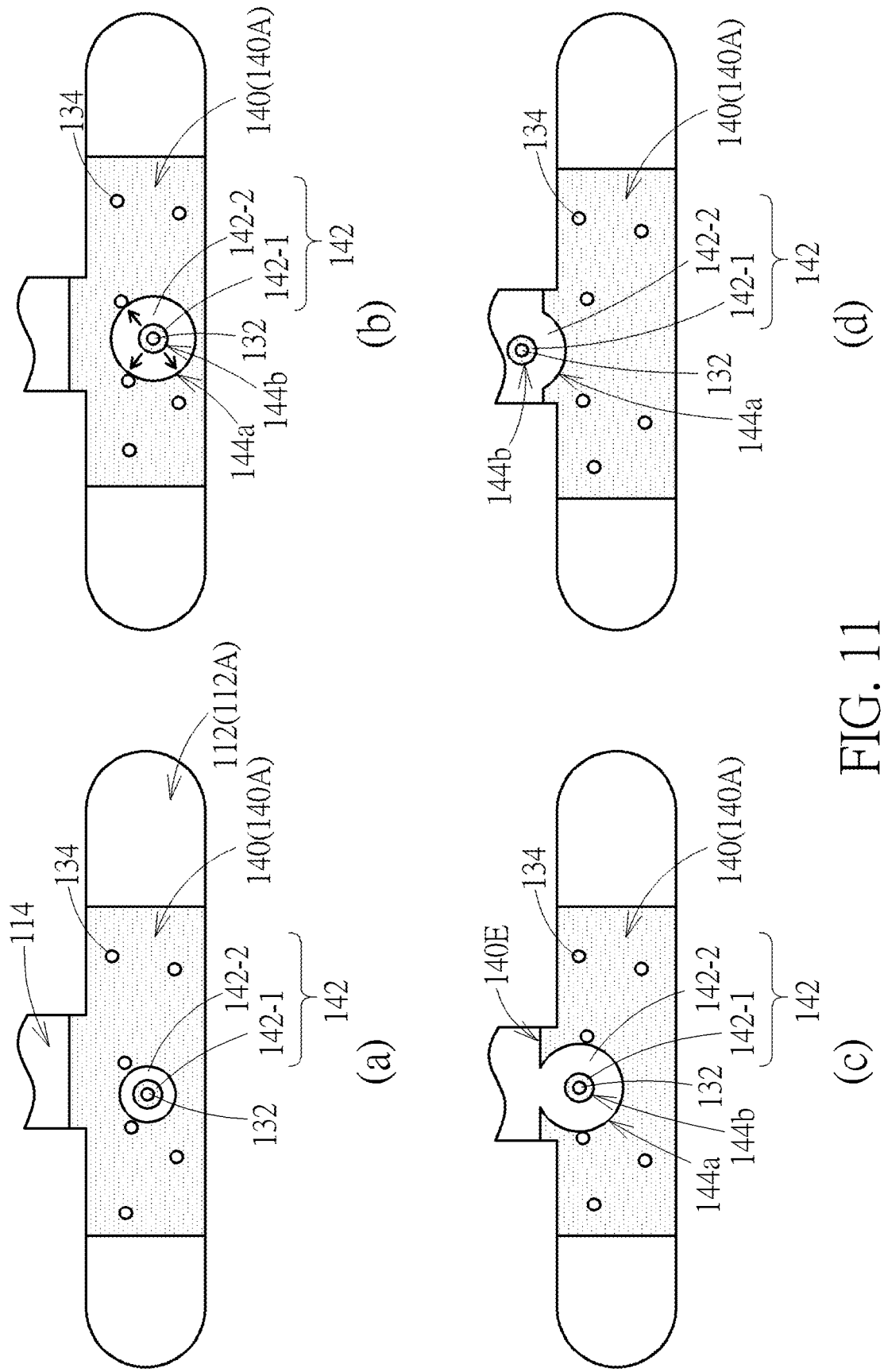
FIG. 11 is a schematic diagram showing a method of manipulating bio-particles in a device by using image-manipulated electric force according to another embodiment of the present disclosure.

FIG. 11 is a schematic diagram showing a method of manipulating bio-particles in a device by using image-manipulated electric force according to another embodiment of the present disclosure. In step (a), the cell 132 may be identified and located by a microscope when it flows to a predetermined region. In order to identify the cell 132, the to-be-sorted cell 132 and unwanted cells 134 may be stained with different fluorescent dyes before they enter the main channel. Thus, the fluorescence emitting from the cell 132 may be different from the fluorescence emitting from the cell 134. The cell 132 may be distinguished from other cells 134 by using fluorescence microscope which detects the fluorescence emitting from cells 132 and 134. Once the cell 132 is identified and located, an alternating electrical field may be applied across two opposing transparent conductive electrodes, and a light may be illuminate on the photosensitive material so as to generate a light zone 140 in the main channel 112. Also, the light pattern 142 including the inner light zone 142-1 and an outer dark zone 142-2 is illuminated on the photosensitive material where the cell 132 exists. Then, in step (b), the outer dark zone 142-2 of the light pattern 142 may be expanded. Because of the electrical field gradient generated at the outer edge 144*a* of the outer dark zone 142-2, cells 134 near the outer edge 144*a* of the light pattern 142 may be pushed farther from the center of the light pattern 142 during the process of expanding the outer dark zone 142-2. Afterwards, in step (c), the cell 132 may be moved toward a side channel by moving the light pattern 142. During the movement of the light pattern, light pattern 142 may repel all cells 134 encountering the outer edge 144*a* of the moving light pattern 142. Therefore, the cells 134 outside the light pattern 142 may not be able to move toward the side channel 114. Finally, in step (d), the cell 132 may penetrate the edge 140E of the light zone 140 and enter the side channel 114. It should be noted that, since there is an electrical field gradient at the edge 140E of the light zone 140, the cells 134 may also be repelled by the electrical field gradient at the edge 140E and thus not enter the side channel along with the cell 132.

Figure 12:
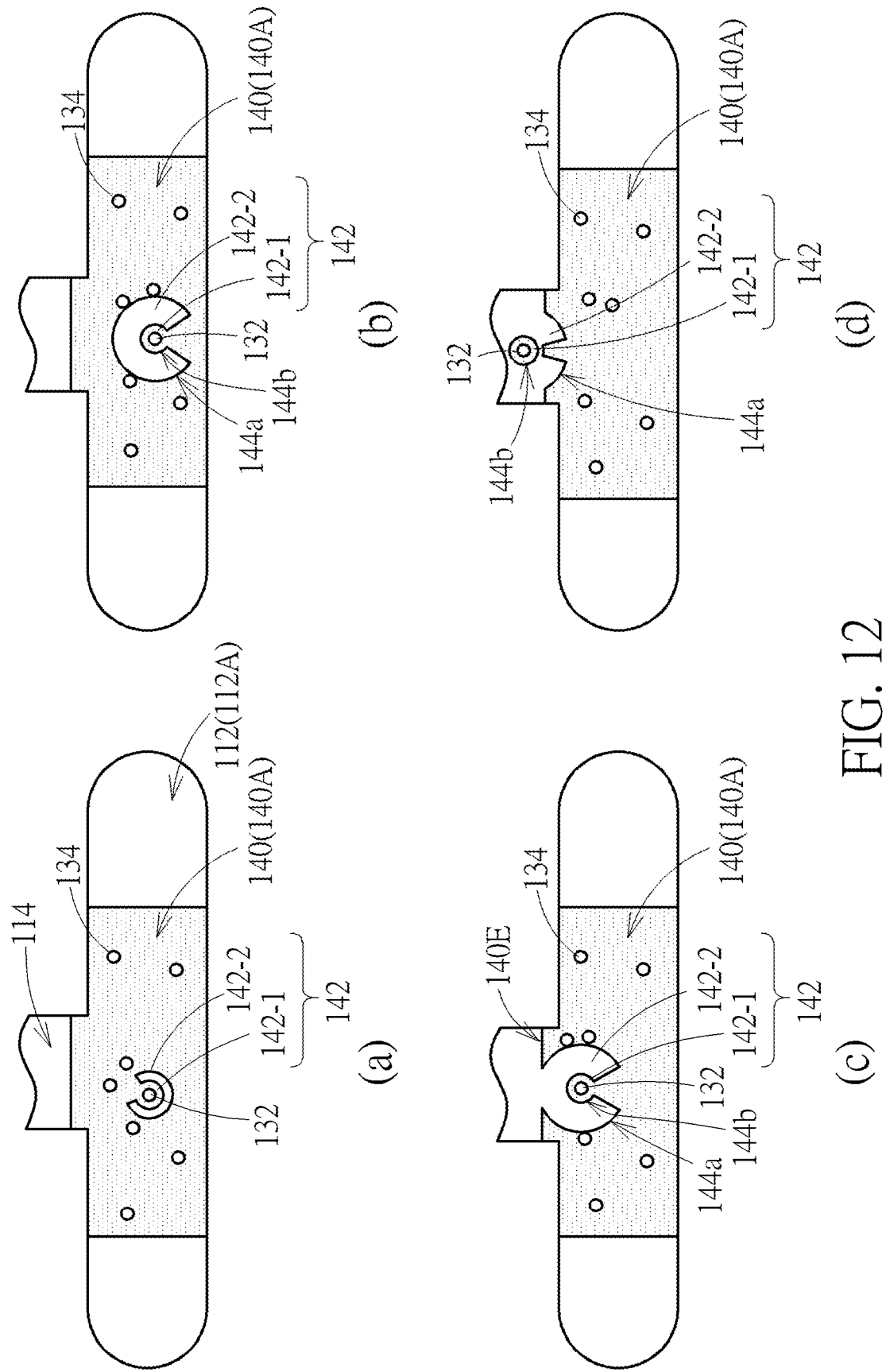
FIG. 12 is a schematic diagram showing a method of manipulating bio-particles in a device by using image-manipulated electric force according to still another embodiment of the present invention.

FIG. 12 is a schematic diagram showing a method of manipulating bio-particles in a device by using image-manipulated electric force according to still another embodiment of the present disclosure. The method describing in FIG. 12 is similar to that described in FIG. 11, the main difference is that the outer dark zone 142-2 of the light pattern 142 is of an incomplete ring. That is to say, the cell 132 overlapping the light pattern 142 is not fully enclosed by the outer dark zone 142-2. During the movement of the light pattern 142, in step (b), the outer dark zone 142-2 may rotate property to prevent the cells 134 from being swallowed into the inner light zone 142-1 through the opening of the outer dark zone 142-2 in the process of moving the light pattern 142. Since other steps of this embodiment are similar to those described in the embodiment of FIG. 11, the detailed description of these steps is therefore omitted for the sake of brevity. It should be noted that, the sequence of the steps of moving the light pattern 142, rotating the outer dark zone 142-2, and expanding the outer dark zone 142-2 may be altered to meet different requirements. Besides, these three steps may also be carried out concurrently as an alternative.

Figure 13:
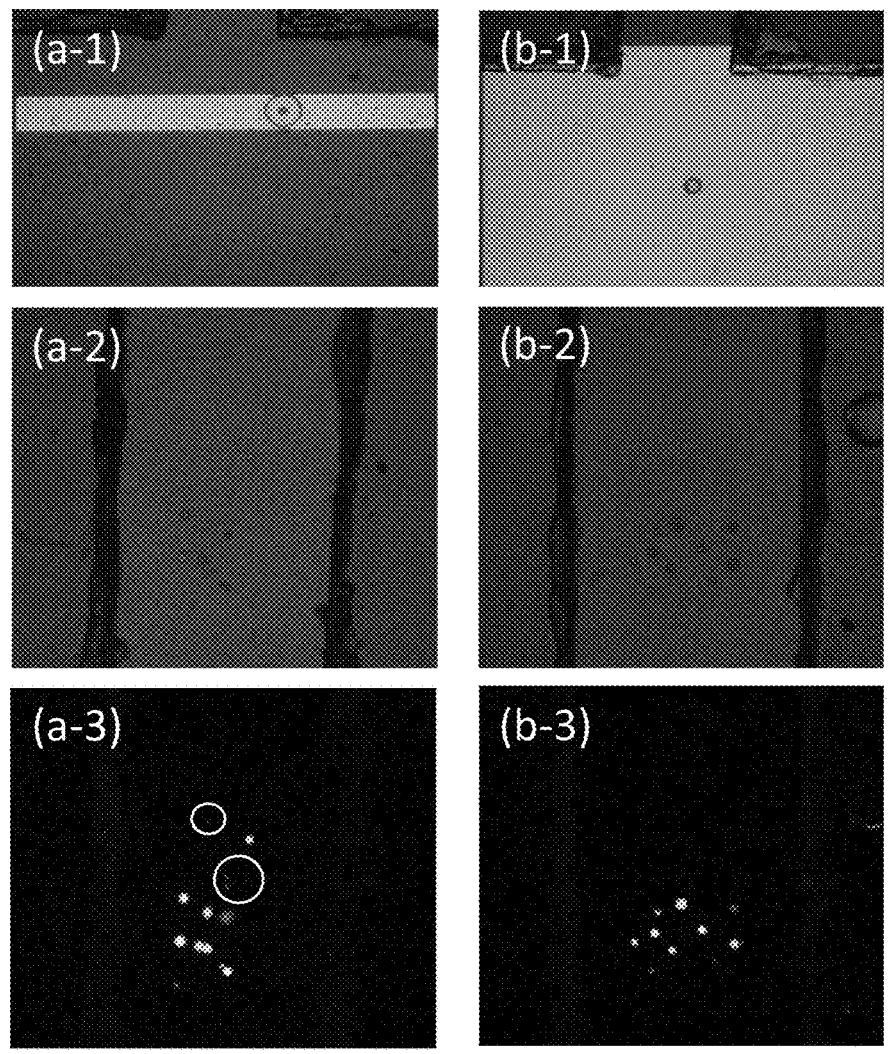
FIG. 13 shows images of optical and fluorescence microscopes according to comparative and exemplary examples.

Compared with the sorting method disclosed in U.S. Pat. No. 2017/0297036, the sorting method described in FIGS. 11 and 12 of the present application is much more efficient and accurate. Please refer to Table 1 below and FIG. 13. Photographs (a-1) to (a-3) of FIG. 13 correspond to sorting method disclosed in US 2017/0297036. Photographs (a-1) and (a-2) are images taken by an optical microscope, which show that bio-particles (refer to "dots") are sorted into a collection channel. However, as shown in photograph (a-3) which is observed through a fluorescence microscope, many unwanted bio-particles (refer to "encircled bright dots") are also sorted into the collection channel. Photographs (b-1) to (b-3) of FIG. 13 correspond to sorting method disclosed in the present application. Photographs (b-1) and (b-2) are images taken by an optical microscope, which show that bio-particles (refer to "dots") are sorted into a collection channel. Furthermore, as shown in photograph (b-3) which is observed through a fluorescence microscope, none of the unwanted bio-particles are sorted into the collection channel. Therefore, the photographs demonstrate that the sorting accuracy of the present application is much better than that of the conventional techniques.

Besides, according to the results shown in Table 1, for method disclosed in US 2017/0297036, the sorting time per cell is about 139.2 (s) and the accuracy is about only 60.4%. The low accuracy means that the unwanted cells are not swept away completely by the light bar and thus some of the unwanted cells may flow into the colleting region along with the cells to be sorted. In contrast, according to the sorting method disclosed in the present disclosure, the sorting time per cell is reduced to about 72.1 (s) and the accuracy is increased up to 100%.

TABLE 1

|  | Comparative Examples | | | Exemplary Examples | | |
| --- | --- | --- | --- | --- | --- | --- |
|  | 1 | 2 | 3 | 1 | 2 | 3 |
| Identified bio-particles (#) | 10 | 10 | 10 | 10 | 10 | 10 |
| unwanted bio-particles (#) | 5 | 8 | 7 | 0 | 0 | 0 |
| AVG purity (%) | | 60.4 ± 5.7 | | | 100 | |
| AVG Separation time per bio-particle (sec) | | 139.2 ± 32. | | | 72.1 ± 12.2 | |

Figure 14:
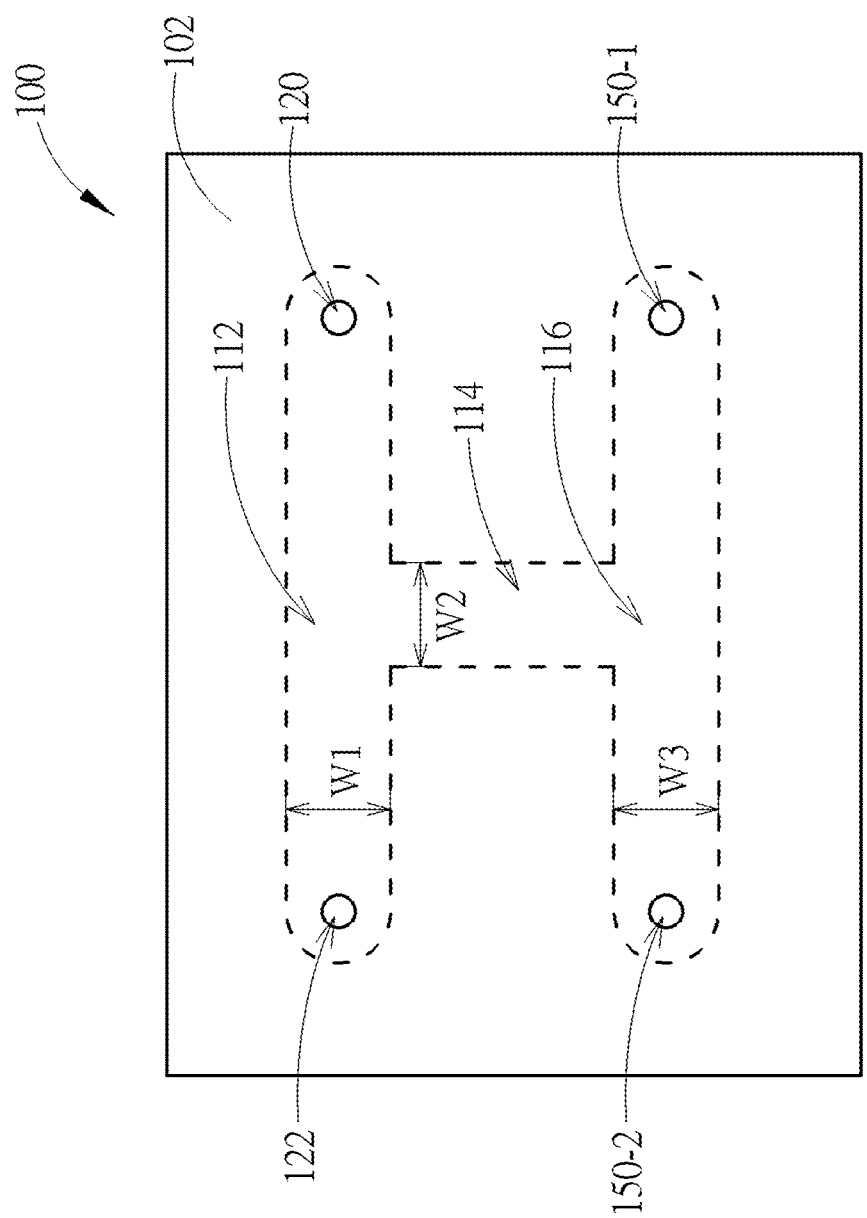
FIG. 14 is a schematic top view of a device having several fluidic channels according to one embodiment of the present disclosure.
Figure 15A:
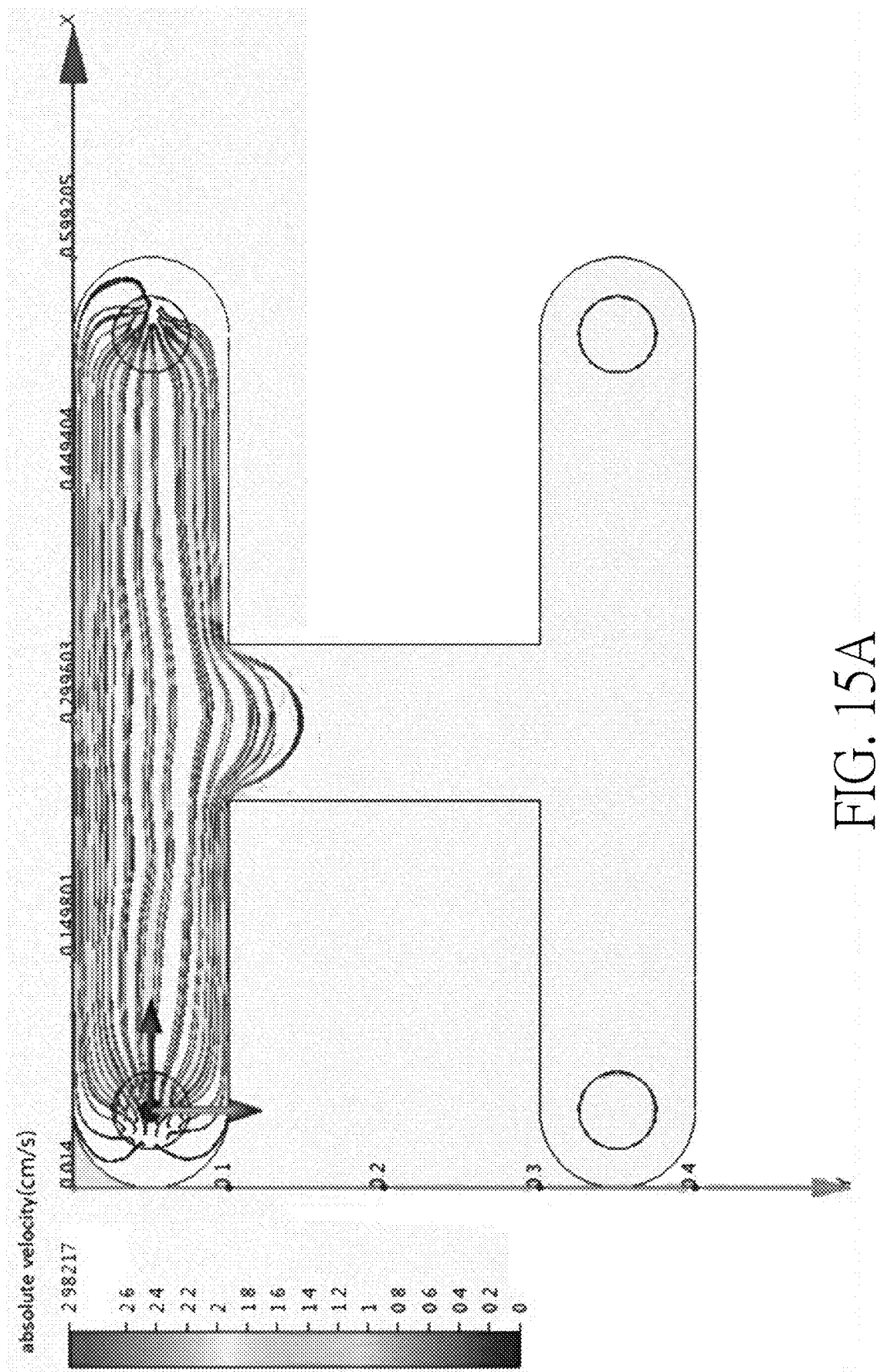
FIG. 15A is experiment data verifying an operating result of a sorting device where the width ratio of a main channel, a side channel and a collection channel is 1:1:1.
Figure 15B:
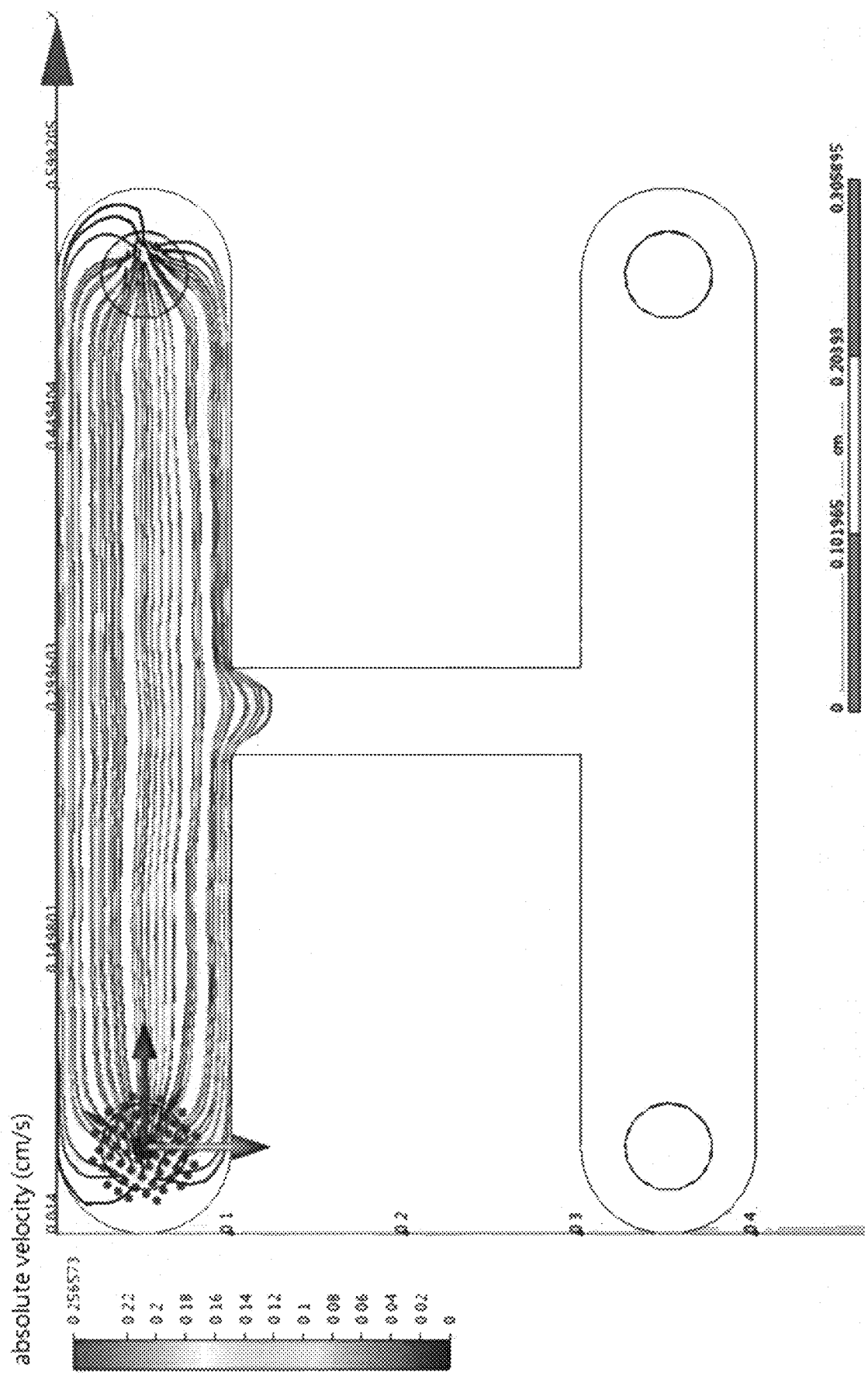
FIG. 15B is experiment data verifying an operating result of a sorting device where the width ratio of a main channel, a side channel and a collection channel is 2:1:2.
Figure 15C:
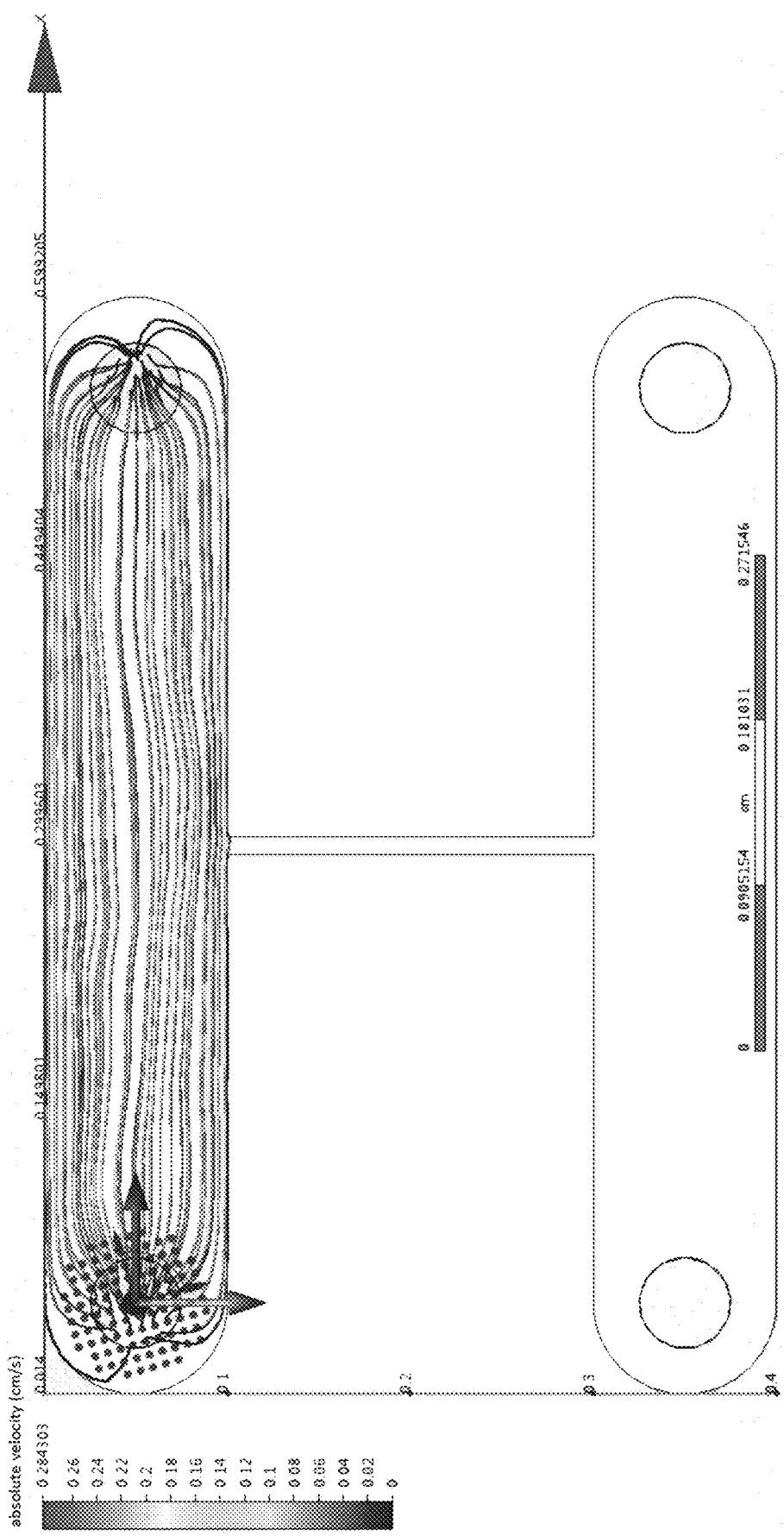
FIG. 15C is experiment data verifying an operating result of a sorting device where the width ratio of a main channel, a side channel and a collection channel is 10:1:10.

FIG. 14 is a schematic top view of a device having several fluidic channels according to one embodiment of the present disclosure. The device 100 shown in FIG. 14 is similar to that shown in FIG. 1, the main difference is that the device shown in FIG. 14 further includes other microfluidic channels, such as a side channel 114 and a collection channel 116. Two ends of the side channel 114 may be respectively connected to the main channel 112 and collection channel 116. During the operation of the device 100, the to-be-sorted cells may be sorted from the main channel 112 through the side channel 114 to the collection channel 116 and temporarily stored in the collection channel 116. When the number of the cells being stored in the collection channel 116 exceeds a certain value or anytime by the user's own will, these cells may be further flow out by buffer from a buffer inlet hole 150-1 to the collection channel 116 and drained through a collection hole 150-2 to a test tube. Besides, the width ratio of the main channel, the side channel and the collection channel are in a range of 1:1:1 to 10:1:10, such as 1:1:1, 2:1:2 and 10:1:10, but not limited thereto. The advantage of the present embodiment is that the cell to be sorted may be stored in the collection channel 116 temporarily so that the sorting process conducted in the main channel 112 may be carried out consecutively without being interrupted. Besides, the device 100 may be used to sort different types of cells. For example, in a first round of sorting process, a group of cells of the same kind may be collected in the collection channel 116 and then flow out to the test tube. Then, in a second round of sorting process, a group of other kind cells may be collected in the collection channel 116 and then flowed out to the test tube. FIG. 15 shows an operating result of sorting devices having different width ratio of the main channel, the side channel and the collection channel. The result shown in FIG. 15 demonstrates that when the width ratios are designed within the above range according to the experiment, the fluid in the main channel 112 and the collection channel 116 may not flow into the side channel 114 when the fluid flows in the main channel 112 and/or collection channel 116, thus to prevent unwanted cells flowing into the collection channel 116 from the main channel 112, and vice versa.

Figure 16:
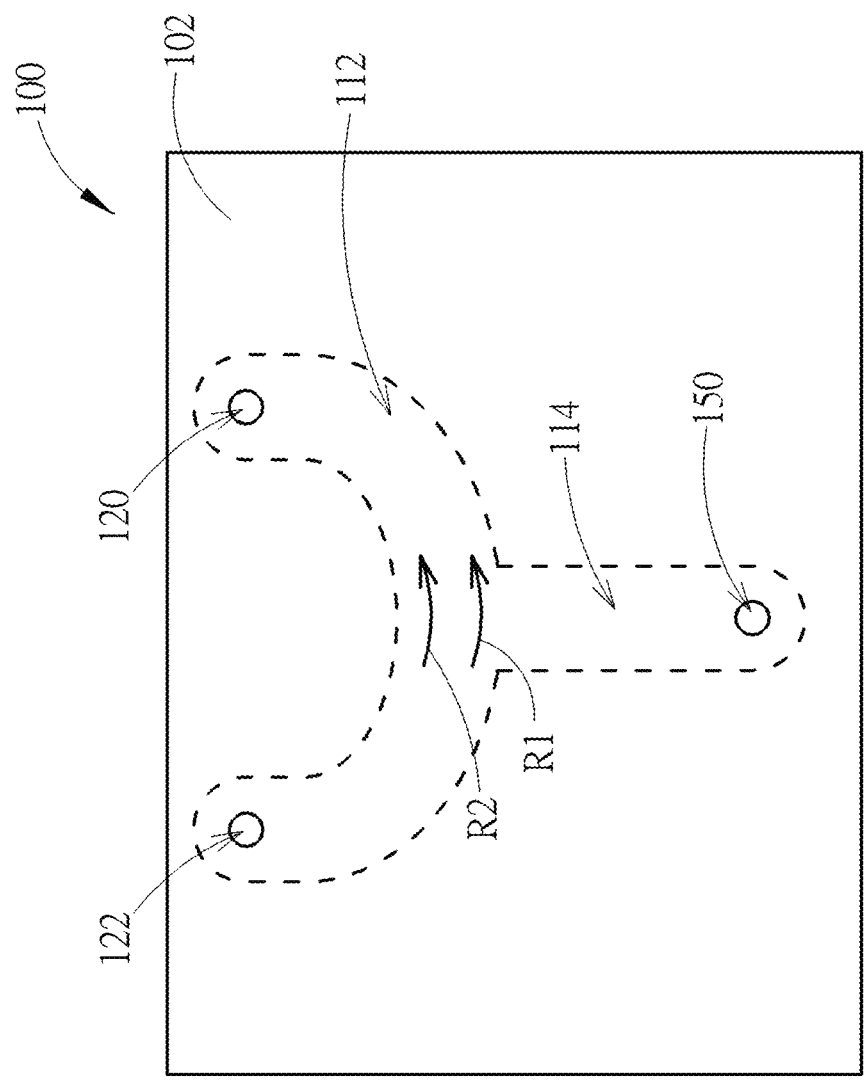
FIG. 16 is a schematic top view of a device having a curved main channel according to another embodiment of the present disclosure.
Figure 17:
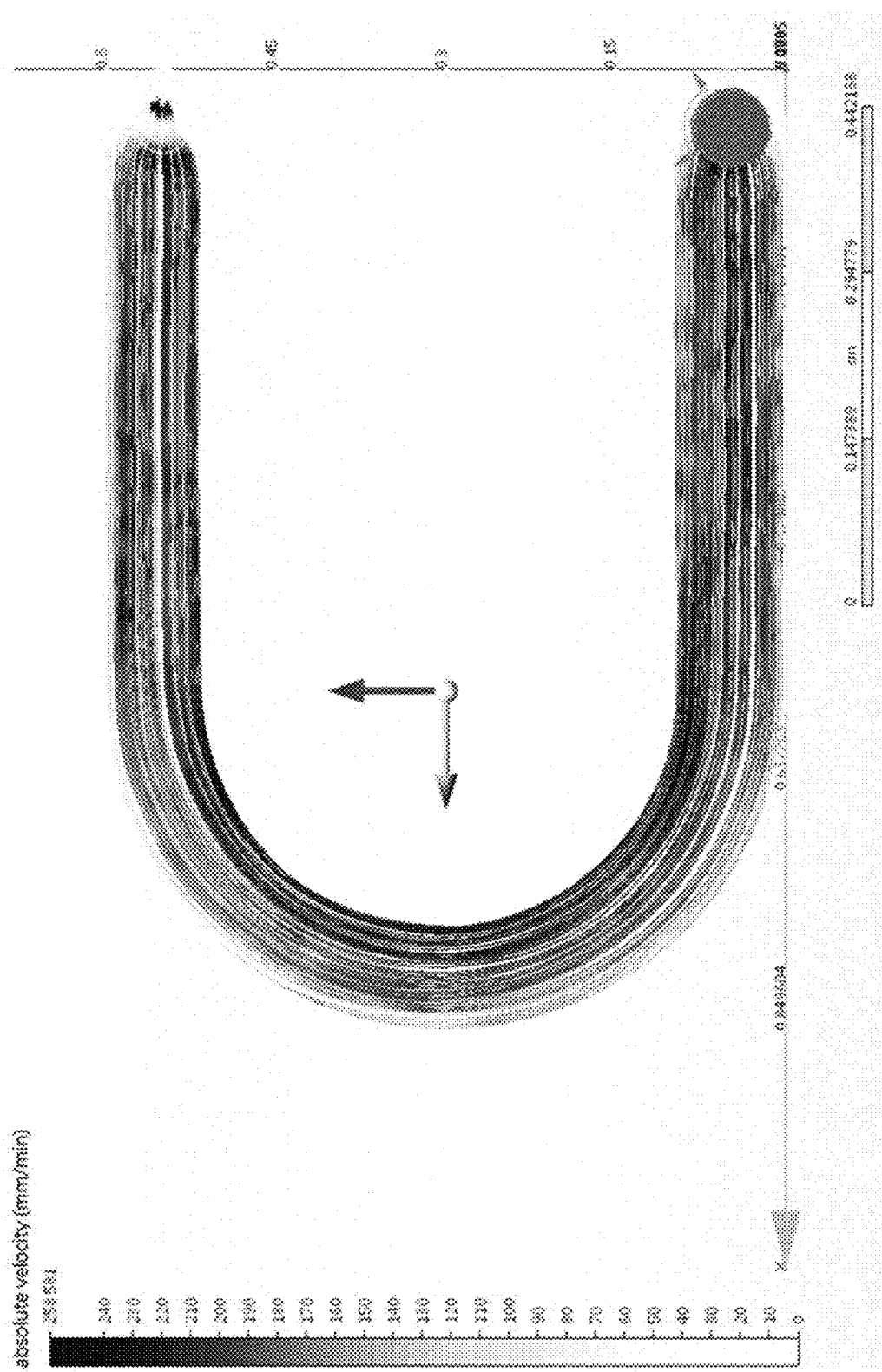
FIG. 17 is experiment data verifying the flow rates at different locations of a curved main channel.

FIG. 16 is a schematic top view of a device having a curved main channel according to another embodiment of the present disclosure. The device 100 shown in FIG. 16 is similar to that shown in FIG. 1, the main difference is that the device shown in FIG. 16 further includes a curved main channel 112 and a side channel 114. One end of the side channel 114 is connected to an apex of the curved main channel 112. According to this embodiment, experiment data shows that the flow rate R1 on the outer curve of the curved main channel 112 is slower than the flow rate R2 on the inner curve of the curved main channel 112. For example, for fluid has a linear flow rate of $9 \times 10^{-9}$ mm/min, the flow rate R1 may be $1.7 \times 10^{-12}$ mm/min and the flow rate R2 may be $4.7 \times 10^{-9}$ mm/min. Therefore, when the cells are sorted at the intersection of the curved main channel 112, the sorting process may be more effective due to the slower flow rate in this region and it is more likely to prevent fluid in the curved main channel 112 from flowing into the side channel 114. The experiment data is shown in FIG. 17, which demonstrates that the flow rate close to the outer curve of the curved main channel is slower than the flow rate close to the inner curve of the curved main channel.

Figure 18:
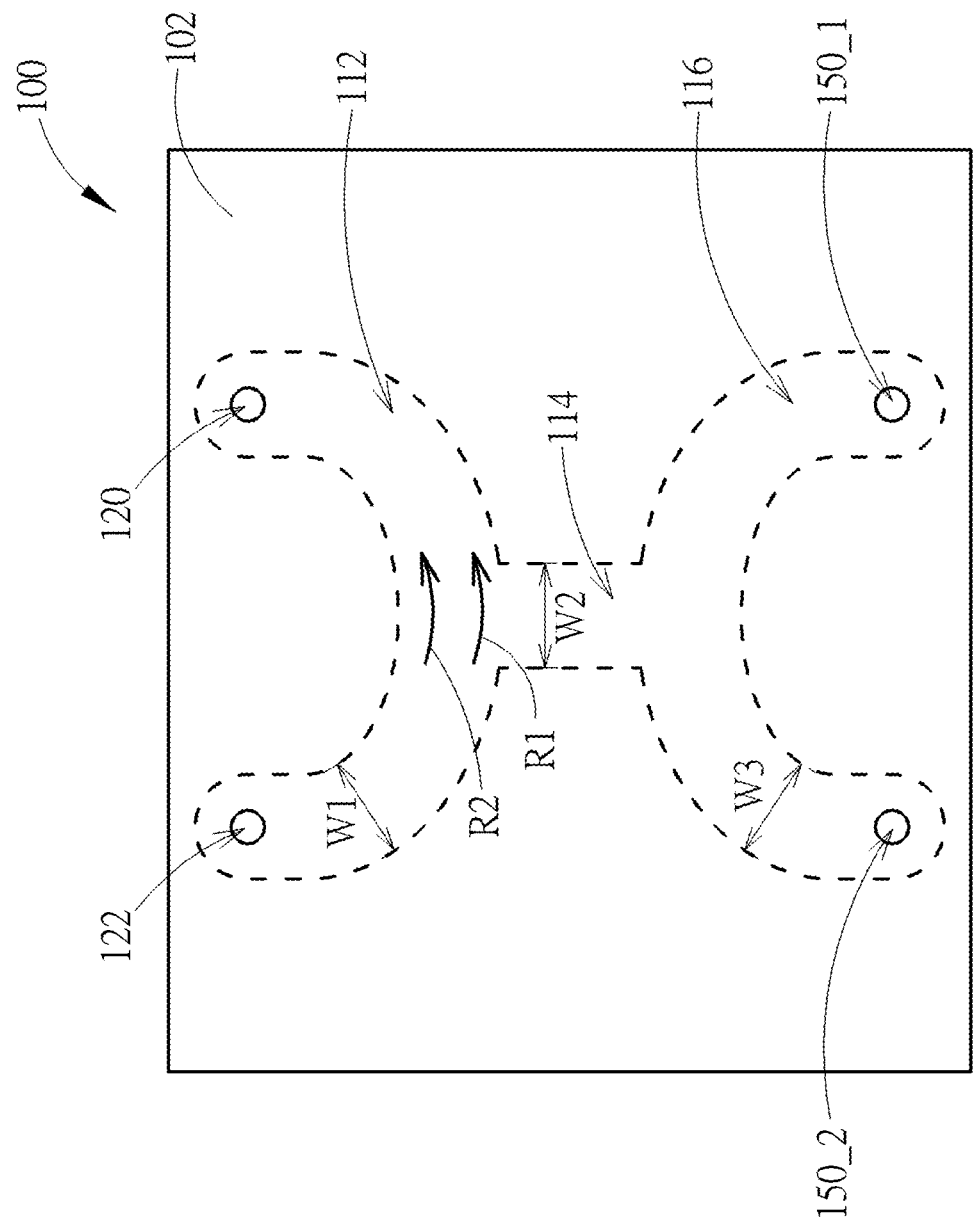
FIG. 18 is a schematic top view of a device having a curved main channel and a curved collection channel according to still another embodiment of the present disclosure.

FIG. 18 is a schematic top view of a device having a curved main channel and a curved collection channel according to still another embodiment of the present disclosure. The device 100 shown in FIG. 18 may be regarded as an integration of the structures shown in FIG. 14 and FIG. 16. The advantage of embodiment shown in FIG. 18 is that the cell to be sorted may be stored in the curved collection channel temporarily so that the sorting process conducted in the main channel 112 may be carried out consecutively without being interrupted. Also, the device 100 may be used to sort different types of cells. Besides, the flow in the main channel 112 and the collection channel 116 may be laminar flow, which means that fluid in the main channel 112 and the collection channel 116 may not flow into the side channel 114 during the flow of the fluid, thus to prevent unwanted cells flowing into the collection channel 116 from the main channel 112, and vice versa. Furthermore, since the flow rate R1 on the outer curve of the curved main channel 112 is slower than the flow rate R2 on the inner curve of the curved main channel 112, the sorting process may be more effective when the cells are sorted at the intersection of the curved main channel 112 and the side channel 114.

Figure 19:
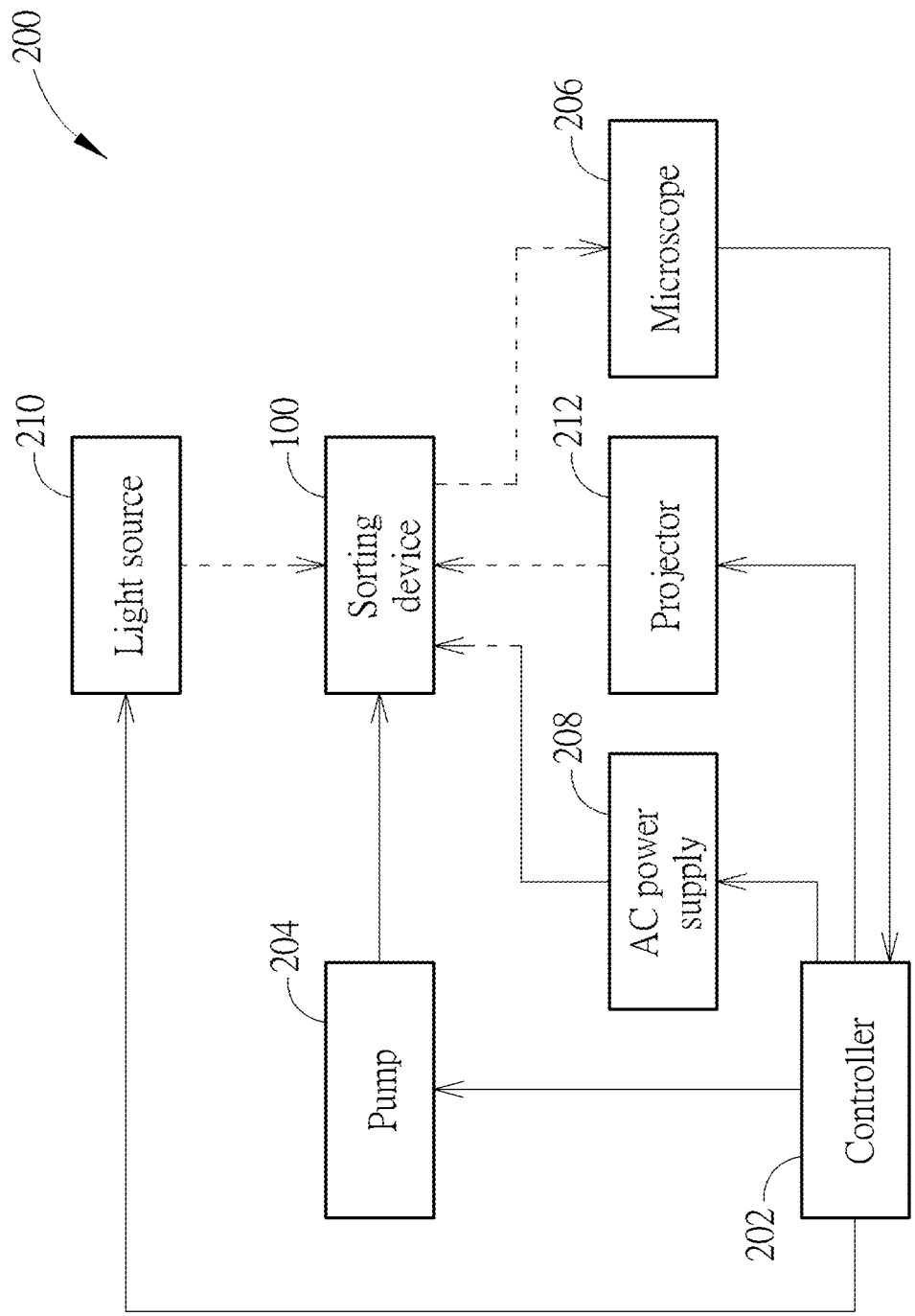
FIG. 19 is a schematic system configuration for sorting bio-particles from fluid heterogeneous mixture according to one embodiment of the present disclosure.

FIG. 19 is a schematic system configuration for sorting bio-particles from fluid heterogeneous mixture according to one embodiment of the present disclosure. Referring to FIG. 19, a system configuration 200 for sorting bio-particles from fluid heterogeneous mixture may include a sorting device, such as the device 100 disclosed above, and other mechanical, electronic or optical components. The mechanical, electronic or optical components, for example, may include a controller 202, a pump 204, a microscope 206, an AC power supply 208, a light source 210, and a projector 212, but not limited thereto. The controller 202 may be a central processing unit (CPU) or other suitable controlling units electrically coupled to the pump 204, the microscope 206, the AC power supply 208, the light source 210, and the projector 212, and the controller 202 may be configured to receive, process, and transmit electrical signals. The pump 204 may be a micro pump, such as a suction-type syringe pump, which is connected to the sorting device 100 and configured to let the fluid containing bio-particles flow in the channel of the sorting device 100. The light source 210 may be a light emitting device configured to illuminate light of required wavelength onto the channel of the sorting device 100. The projector 212 may be a digital projector configured to generate a light pattern, such as a light pattern composed of an inner light zone and an outer dark zone, and illuminate the light pattern onto the channel of the sorting device 100. The microscope 206 may be a CCD-equipped fluorescence microscope configured to observe the manipulation of the bio-particles in the channel of the sorting device 100.

Figure 20:
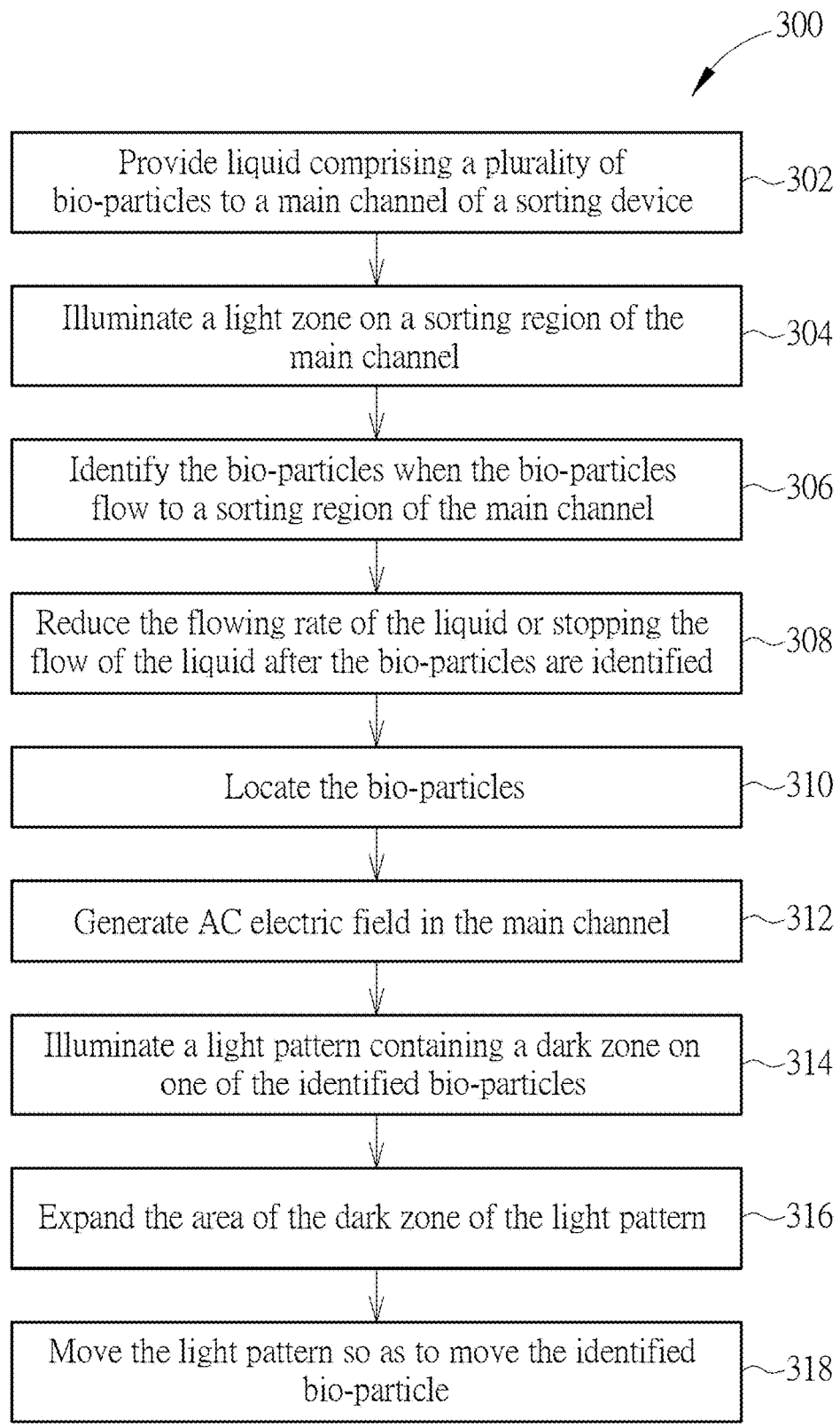
FIG. 20 is a flow chart illustrating a method of operating a device for sorting bio-particles according to one embodiment of the present disclosure.

FIG. 20 is a flow chart illustrating a method of operating a device for sorting bio-particles according to one embodiment of the present disclosure. Referring to FIG. 19 and FIG. 20, in step 302, liquid containing bio-particles is provided to a main channel of a sorting device. According to one embodiment of the present disclosure, a liquid mixture containing bio-particles, such as cells, and liquid medium may flow in the channel of the device 100 by using the pump 204. The liquid mixture may flow into the device 100 through an inlet, pass through a sorting region of the main channel, and flow out of the device 100 through an outlet. Then, in step 304, a light zone is illuminated on the sorting region of the main channel when the liquid mixture is transported in the main channel. According to one embodiment of the present disclosure, a light zone may be generated in the main channel by using the light source 210. Afterward, in step 306, the bio-particles flowing into the sorting region of the main channel may be identified by using the microscope 206. According to one embodiment of the present disclosure, the microscope 206 may be a fluorescence microscope being able to detect the fluorescence emitting from the stained bio-particles so as to determine the types of the bio-particles in the sorting region. Then, in step 308, the flowing rate of the liquid mixture may be slowed down or down to zero by using the controller 202 to transmit a command signal to the pump 204. In step 310, the positions of the bio-particles in the sorting region may be determined. According to one embodiment of the present disclosure, for the purpose of operation efficiency, only the positions of the to-be-sorted bio-particles in the sorting region may be determined, and the positions of the unwanted bio-particles may not be determined. Once the bio-particles, or at least the to-be-sorted bio-particles, are identified and located, in step 312, an alternating electric field may be applied to the sorting region of the main channel by using the AC power supply 208. According to one embodiment of the present disclosure, by applying the alternating electric field, the bio-particles in the sorting region may be anchored at their original locations and would not diffuse to other locations. Then, in step 314, a light pattern containing a dark zone is illuminated on at least one of the identified bio-particles, or at least one of the to-be-sorted bio-particles, by using the projector 212. According to one embodiment of the present disclosure, an electric field gradient, which is the key to generate a dielectrophoresis (DEP) force, may be generated near the edges of the dark zone so that the identified bio-particle overlapping the light pattern may be manipulated by moving the light pattern. Subsequently, in step 316, the dark zone may be expanded so that the bio-particles outside the light pattern and near the outer edge of the dark zone may be pushed farther from the center of the light pattern. Afterwards, in step 318, the identified bio-particle, or the to-be-sorted bio-particle, overlapping the light pattern may be manipulated by moving the light pattern. During the movement of the light pattern, the light pattern may repel all bio-particles encountering the outer edge of the moving light pattern. Subsequently, the identified bio-particle may penetrate the edge of the light zone in the sorting region and enter a target channel, such as a side channel, of the device 100. By using the method 300 disclosed above, the to-be-sorted bio-particles may be collected to a predetermined region and precisely separated from the unwanted bio-particles. Although steps 302-318 are disclosed and arranged in a specific order, one of ordinary skill in the art would understand that any of the steps illustrated in method 300 may be combined, modified, or deleted where appropriate, and additional steps may also be added to those shown in the flowchart. Moreover, the described steps may be performed in any suitable order without departing from the scope of the invention.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:
1. A device for sorting bio-particles by image-manipulated electric force, comprising:
   a first substrate comprising a first conductive electrode;
   a second substrate comprising a second conductive electrode, wherein the second conductive electrode is disposed opposite the first conductive electrode;
   a fluidic channel disposed between the first conductive electrode and the second conductive electrode;

one or more photosensitive layers conformally disposed on at least one surface of either or both of the first conductive electrode and the second conductive electrode;

an inlet hole disposed in the first conductive electrode and in the first substrate, wherein the inlet hole comprises a first opening close to the fluidic channel and a second opening away from the fluidic channel, and the surface area of the first opening is greater than the surface area of the second opening;

an outlet hole disposed in the first conductive electrode and in the first substrate, wherein the outlet hole comprises a third opening close to the fluidic channel and a fourth opening away from the fluidic channel, and the surface area of the third opening is greater than the surface area of the fourth opening; and at least two cylinder-shaped through holes disposed in the first substrate and connected respectively to the second opening of the inlet hole and the fourth opening of the outlet hole.

2. The device of claim 1, further comprising an outlet hole disposed in the second conductive electrode and in the second substrate, wherein the outlet hole comprises a third opening close to the fluidic channel and a fourth opening away from the fluidic channel, and the surface area of the third opening is greater than the surface area of the fourth opening.

3. The device of claim 2, wherein the inlet hole comprises cross-sectional areas gradually reduced from the first opening to the second opening, and the outlet hole comprises varying cross-sectional areas gradually reduced from the third opening to the fourth opening.

4. The device of claim 1, wherein the first substrate and the second substrate respectively comprise an inner surface, and the first conductive electrode and the second conductive electrode are respectively on the inner surfaces.

5. The device of claim 1, wherein one of the photosensitive layers is conformally disposed on the surface of the first conductive electrode, and another one of the photosensitive layers is conformally disposed on the surface of the second conductive electrode.

6. The device of claim 1, wherein the fluidic channel comprises a main channel and a side channel, and one end of the side channel is connected to the main channel.

7. The device of claim 6, wherein the fluidic channel further comprises a collection channel connected to another end of the side channel, wherein a ratio of a channel width of the main channel to a channel width of the side channel is between 1:1 to 10:1, wherein a ratio of the channel width of the side channel to a channel width of the collection channel is between 1:1 to 1:10.

8. The device of claim 1, wherein the fluidic channel comprises a curved main channel and a side channel, and one end of the side channel is connected to an apex of the curved main channel.

9. The device of claim 8, wherein the fluidic channel further comprises a collection channel connected to another end of the side channel, wherein a ratio of a channel width of the main channel to a channel width of the side channel is between 1:1 to 10:1, wherein a ratio of the channel width of the side channel to a channel width of the collection channel is between 1:1 to 1:10.

10. The device of claim 1, wherein the fluidic channel is a semipermeable channel configured to let ions inside the fluidic channel diffuse out of the fluidic channel.

11. The device of claim 1, further comprising an intermediate layer disposed between the first substrate and the second substrate, wherein the fluidic channel is disposed in the intermediate layer, and the intermediate layer is made of a biocompatible material.

12. A method of operating the device of claim 1, wherein the fluidic channel comprises a main channel and a side channel connected to the main channel, and the method comprises the steps of:
    (a) providing a liquid comprising a plurality of bio-particles to the main channel through the inlet hole;
    (b) identifying the bio-particles when the bio-particles flow to a sorting region of the main channel;
    (c) reducing the flowing rate of the liquid or stopping the flow of the liquid after the bio-particles are identified;
    (d) positioning the bio-particles after step (c);
    (e) illuminating a light zone on the sorting region;
    (f) illuminating a light pattern having a dark zone on the sorting region, wherein the light pattern overlaps at least one of the bio-particles, and the dark zone has a luminance darker than a luminance of a region adjacent to the dark zone; and
    (g) moving the light pattern so as to move the bio-particle overlapping the light pattern.

13. The method of claim 12, wherein, in step (e), an area of the light zone is greater than half of an area of the main channel, and the method further comprises the step of:
    (h) expanding an area of the dark zone when the light zone is illuminated on the sorting region.

14. The method of claim 13, further comprising the step of:
    (i) expanding the area of the dark zone until an outer edge of the dark zone reach an edge of the light zone.

15. The method of claim 12, wherein the fluidic channel further comprises a collection channel connected to the side channel, and the method further comprises the step of:
    (j) moving the bio-particle overlapping the light pattern to the collection channel.

16. The method of claim 12, wherein the light zone is illuminated on the sorting region when step (f) is performed.

17. The method of claim 12, after step (d), further comprising the step of:
    (k) providing an alternating electric field to the sorting region when the light zone is illuminated on the sorting region.

18. The method of claim 12, wherein step (d) is performed by using a fluorescence microscope.

* * * * *